(12) United States Patent  (10) Patent No.: US 9,034,415 B2
Maurer et al.  (45) Date of Patent: May 19, 2015

(54) SURGICAL NEEDLE COATINGS AND METHODS

(71) Applicant: ETHICON, INC., Somerville, NJ (US)

(72) Inventors: Robert Maurer, Somerset, NJ (US); S. Neil Bar, Somerset, NJ (US); Eric Hinrichs, Bucks, PA (US); Michael Hamilton, San Angelo, TX (US); Thomas Wilkes, New Brunswick, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 13/790,073

(22) Filed: Mar. 8, 2013

(65) Prior Publication Data

US 2013/0189422 A1  Jul. 25, 2013

Related U.S. Application Data

(60) Division of application No. 12/858,489, filed on Aug. 18, 2010, which is a continuation-in-part of application No. 12/614,669, filed on Nov. 9, 2009, now abandoned.

(51) Int. Cl.
*B05D 3/02* (2006.01)
*B05D 5/00* (2006.01)
*A61M 5/32* (2006.01)
(Continued)

(52) U.S. Cl.
CPC ............ *B05D 5/00* (2013.01); *A61B 17/06066* (2013.01); *A61B 2017/00526* (2013.01); *A61B 2017/00849* (2013.01); *A61L 31/022* (2013.01); *A61L 31/10* (2013.01); *A61L 2400/10* (2013.01);
(Continued)

(58) Field of Classification Search
CPC .............. A61M 5/32; B05D 3/02; B05D 5/00
USPC .................. 427/2.28; 606/222, 223; 420/432; 148/423.281
See application file for complete search history.

(56) References Cited

U.S. PATENT DOCUMENTS 1,944,823 A  1/1934  Lamont
4,256,870 A  3/1981  Eckberg
(Continued)

FOREIGN PATENT DOCUMENTS

JP  2005-306902 A  11/2005
WO  98/32474 A1  7/1998
WO  2007/024270 A1  3/2007

OTHER PUBLICATIONS

Techsil, Momentive SS4044 Primer clear 500mL.*
(Continued)

*Primary Examiner* — Dah-Wei D Yuan
*Assistant Examiner* — Hai Yan Zhang
(74) *Attorney, Agent, or Firm* — Mintz Levin/Boston Office

(57) ABSTRACT

The present invention provides improved medical devices for use in surgical procedures and methods for manufacturing improved medical devices. In some embodiments, the improved medical devices can include improved surgical needles that are capable of being repeatedly passed through tissue using minimal force. More particularly, the improved surgical needles can be manufactured with two or more different coatings that provide the surgical needles with both durability and lubricity for ease of repeated and successive passes through tissue. Improved methods for manufacturing the surgical needles and for providing and applying coatings to the surgical needles are also provided.

10 Claims, 10 Drawing Sheets

(51) Int. Cl.
*A61B 17/06* (2006.01)
*A61L 31/02* (2006.01)
*A61L 31/10* (2006.01)
*B21G 1/00* (2006.01)
*A61B 17/00* (2006.01)

(52) U.S. Cl.
CPC ............. *A61L 2420/08* (2013.01); *B21G 1/006* (2013.01); *A61L 2420/02* (2013.01)

(56) References Cited

U.S. PATENT DOCUMENTS

| | | | |
|---|---|---|---|
| 4,720,521 A | | 1/1988 | Spielvogel et al. |
| 4,806,430 A | | 2/1989 | Spielvogel et al. |
| 5,258,013 A | | 11/1993 | Granger et al. |
| 5,458,616 A | * | 10/1995 | Granger et al. ............... 606/223 |
| 5,463,010 A | * | 10/1995 | Hu et al. ......................... 528/25 |
| 5,536,582 A | | 7/1996 | Prasad et al. |
| 5,645,884 A | | 7/1997 | Harlow, Jr. et al. |
| 5,911,711 A | | 6/1999 | Pelkey |
| 5,985,355 A | * | 11/1999 | Walther et al. ............... 427/2.28 |
| 5,997,517 A | | 12/1999 | Whitbourne |
| 6,018,860 A | | 2/2000 | Smith et al. |
| 6,231,990 B1 | * | 5/2001 | Lin et al. ....................... 428/447 |
| 6,265,016 B1 | * | 7/2001 | Hostettler et al. ........... 427/2.11 |
| 6,306,176 B1 | | 10/2001 | Whitbourne |
| 6,325,853 B1 | | 12/2001 | Hogan et al. |
| 6,335,383 B1 | | 1/2002 | Scopelianos et al. |
| 6,558,409 B1 | * | 5/2003 | Roby ............................ 606/222 |
| 6,656,167 B2 | | 12/2003 | Numao et al. |
| 6,936,297 B2 | | 8/2005 | Roby et al. |
| 7,015,262 B2 | | 3/2006 | Leong |
| 7,028,867 B2 | | 4/2006 | Acum et al. |
| 7,354,628 B2 | | 4/2008 | Steube |
| 2004/0040467 A1 | | 3/2004 | Thomas et al. |
| 2004/0071988 A1 | | 4/2004 | Nawrocki et al. |
| 2004/0086542 A1 | | 5/2004 | Hossainy et al. |
| 2004/0258931 A1 | | 12/2004 | Zamora et al. |
| 2004/0260269 A1 | * | 12/2004 | Assaf ............................ 604/506 |
| 2004/0266302 A1 | | 12/2004 | DiSalvo et al. |
| 2005/0064088 A1 | | 3/2005 | Fredrickson |
| 2005/0158470 A1 | | 7/2005 | Maiorino |
| 2005/0226993 A1 | | 10/2005 | Nawrocki et al. |
| 2005/0240223 A1 | | 10/2005 | Roby et al. |
| 2005/0255249 A1 | | 11/2005 | Schlatterbeck et al. |
| 2006/0190040 A1 | | 8/2006 | Roby |
| 2006/0224237 A1 | | 10/2006 | Furst et al. |
| 2006/0257667 A1 | * | 11/2006 | Yokoyama et al. ........... 428/428 |
| 2007/0128343 A1 | | 6/2007 | Chappa |
| 2007/0149629 A1 | | 6/2007 | Donovan et al. |
| 2007/0254091 A1 | | 11/2007 | Fredrickson et al. |
| 2007/0267464 A1 | | 11/2007 | Vitcak et al. |
| 2007/0299402 A1 | | 12/2007 | Ishii et al. |
| 2008/0071228 A1 | | 3/2008 | Wu et al. |
| 2008/0102192 A1 | | 5/2008 | Johnson et al. |
| 2008/0139683 A1 | | 6/2008 | Flynn et al. |
| 2008/0147117 A1 | * | 6/2008 | Cichocki et al. .............. 606/223 |
| 2008/0277448 A1 | | 11/2008 | Roby et al. |
| 2009/0026291 A1 | | 1/2009 | Shimada |
| 2011/0111116 A1 | | 5/2011 | Maurer et al. |
| 2011/0112565 A1 | | 5/2011 | Maurer et al. |
| 2011/0112566 A1 | | 5/2011 | Maurer et al. |
| 2013/0209664 A1 | | 8/2013 | Maurer et al. |

OTHER PUBLICATIONS

Sigma-Aldrich, Tetraethyl orthosilicate.*
[No Author Listed] 3M Material Safety Data Sheet for HFE-72DE. Nov. 16, 2007, 9 pages.
[No Author Listed] Momentive® Performance Materials Product Description for Product Code Nos. SS4004P, SS4044P, SS4120, SS4155, and SS4179. Retrieved from <http://www.momentive.com/momentiveInternetDoc/MPM/Static%20Files/Documents> on Apr. 27, 2010. 2003-2010, 4 pages.
[No Author Listed] Momentive® Performance Materials Safety Data Sheet for Product Code No. SS4044P. Version 1.6, Mar. 28, 2008, 9 pages.
[No Author Listed] NuSil® Technologies Material Safety Data Sheet for DSP-9769. Oct. 3, 1996, 7 pages.
[No Author Listed] NuSil® Technologies MED-4162 Product Profile. Dec. 2006, 2 pages.
International Search Report. PCT/US2010/53541, dated Dec. 28, 2010.
International Preliminary Report on Patentability mailed May 24, 2012 for Application No. PCT/US2010/053541 (7 Pages).
International Search Report, PCT/US2010/53545, dated Jan. 3, 2011.
International Preliminary Report on Patentability mailed May 24, 2012 for Application No. PCT/US2010/053545 (8 Pages).
International Search Report, PCT/US2010/53552, dated Dec. 21, 2010.
International Preliminary Report on Patentability for Application No. PCT/US2010/053552 mailed May 24, 2012. (8 pages).
"Petroleum ether." 77399 Sigma-Aldrich. Retrieved Feb. 19, 2014.

* cited by examiner

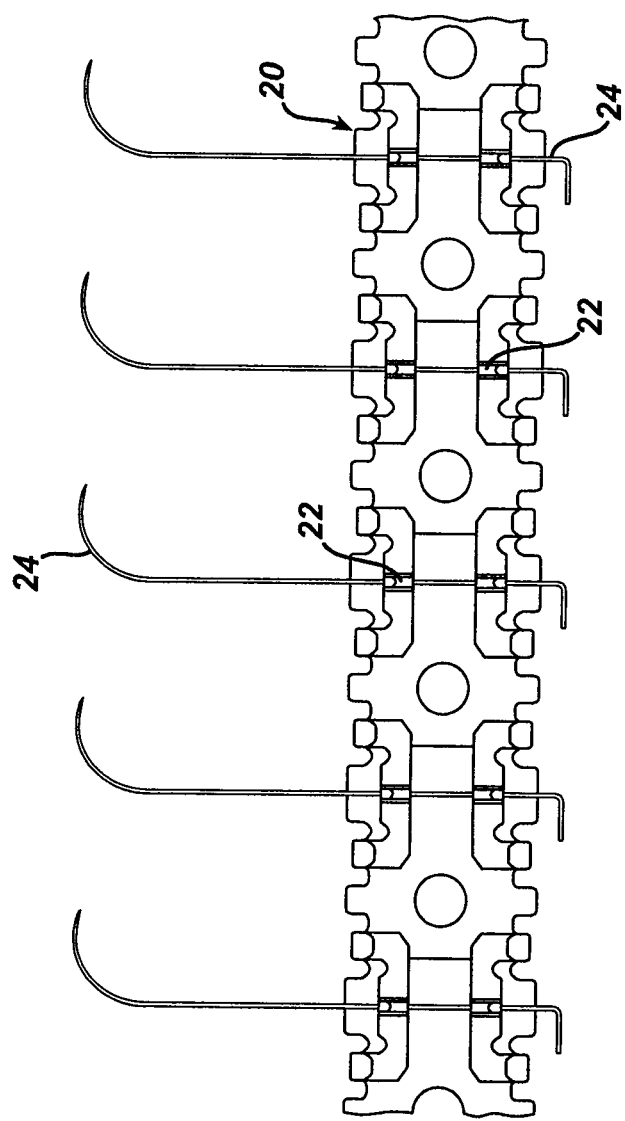

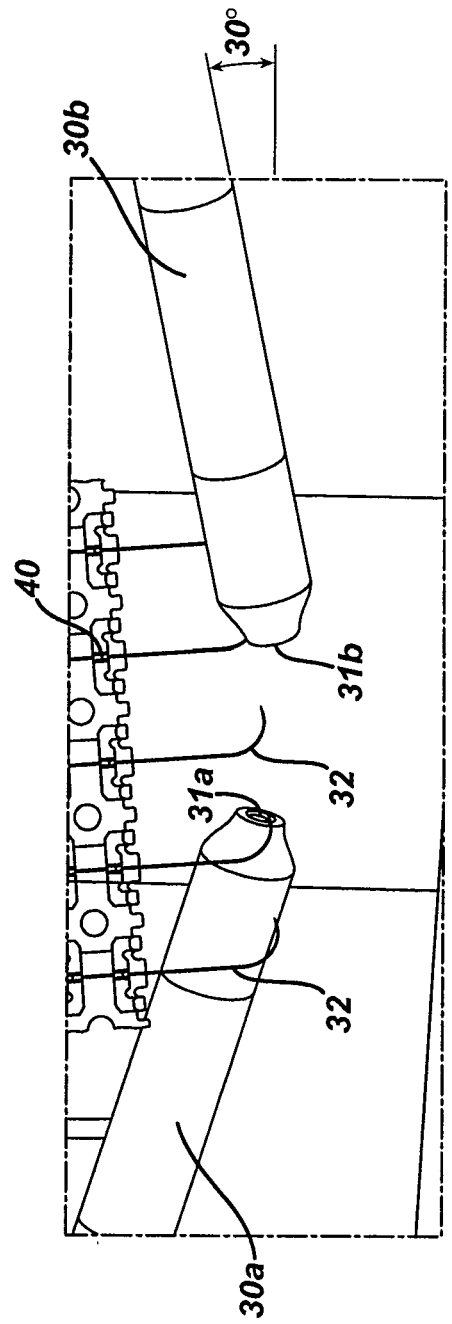

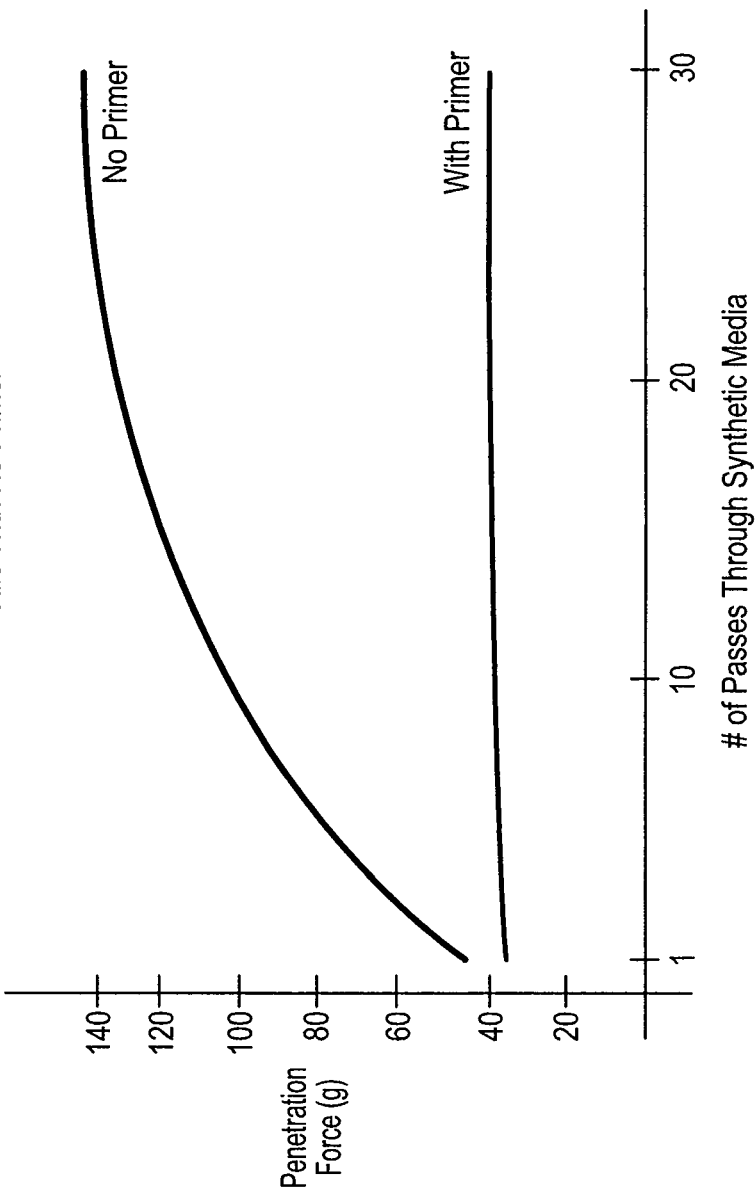

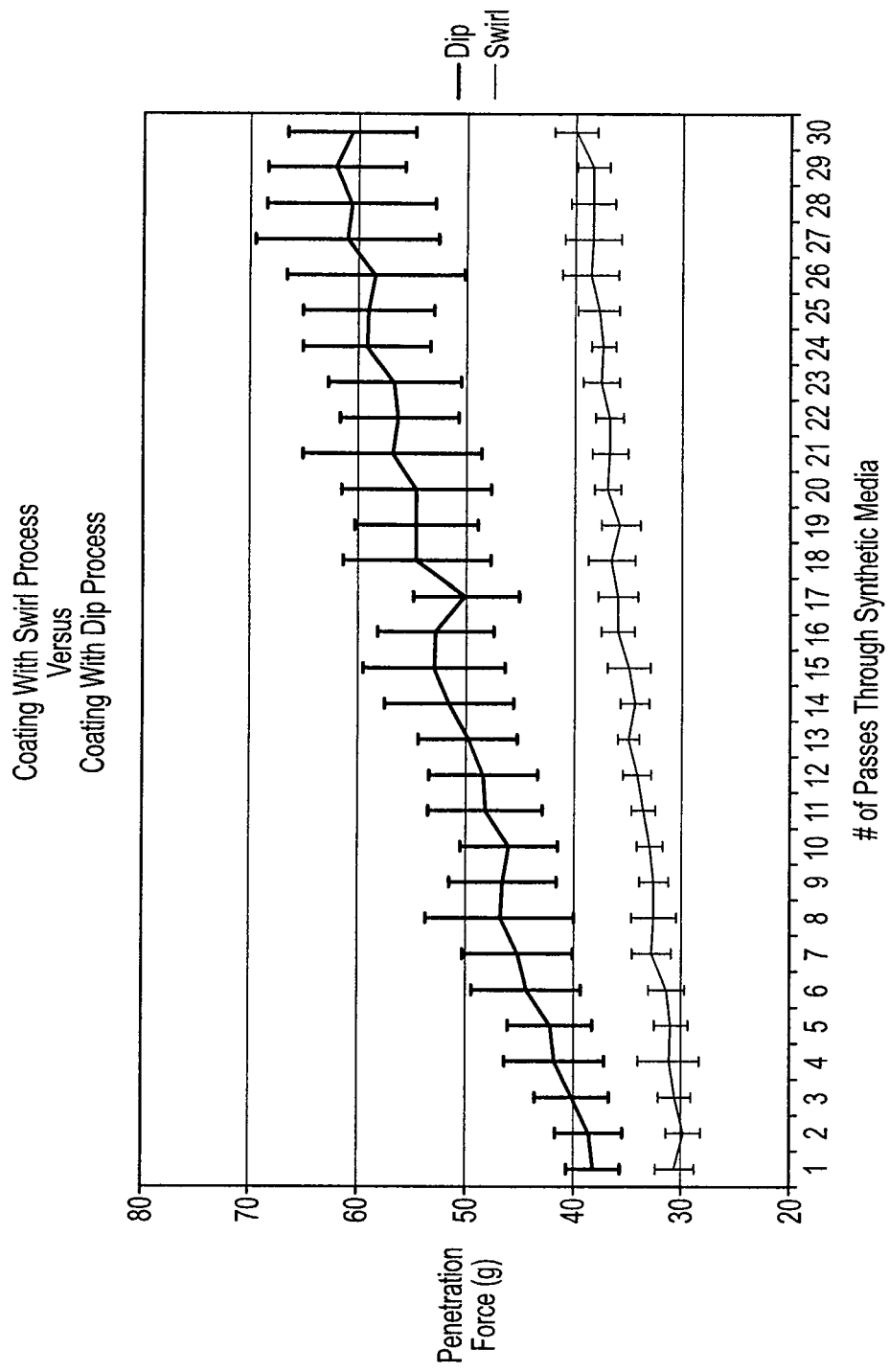

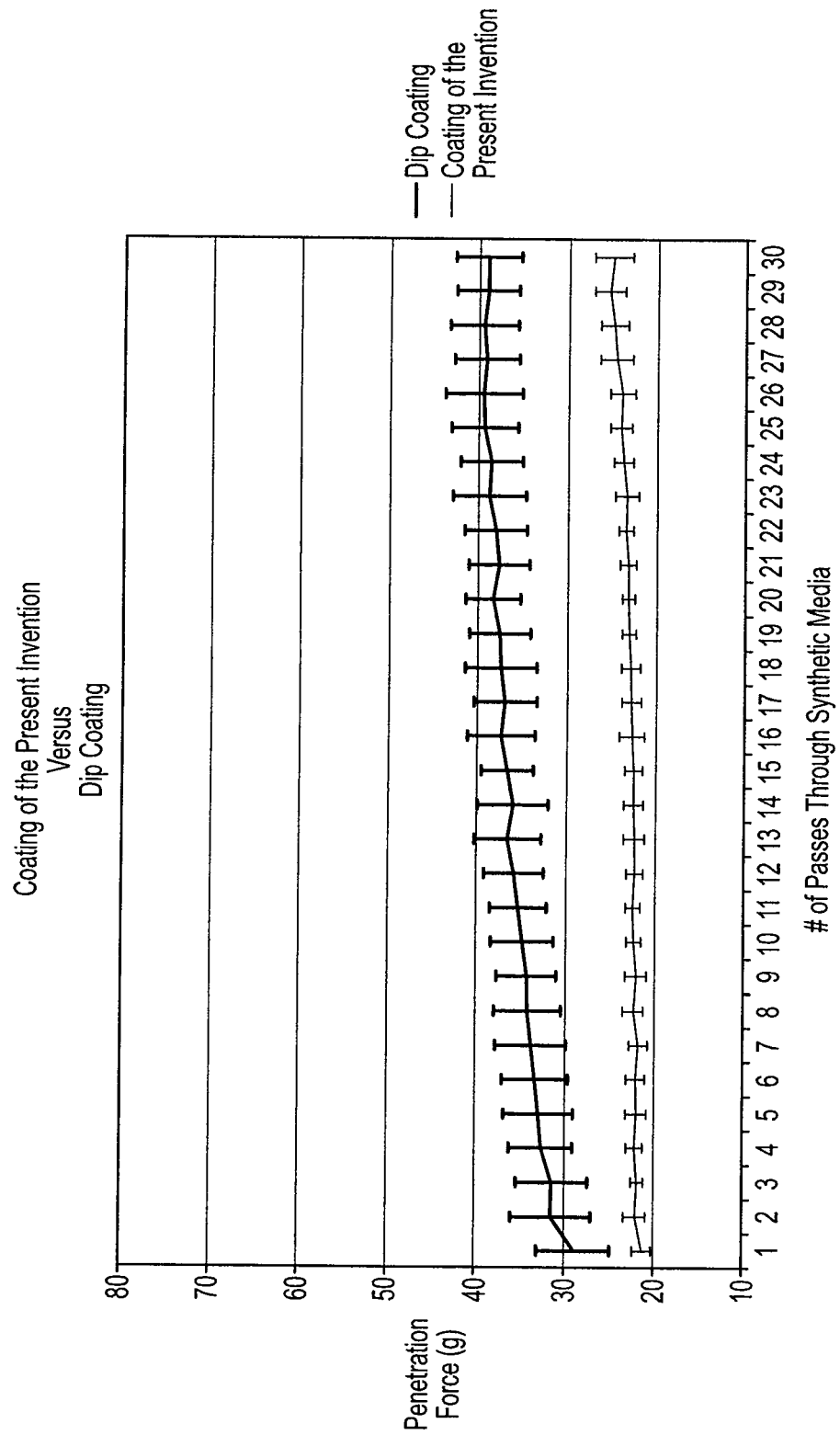

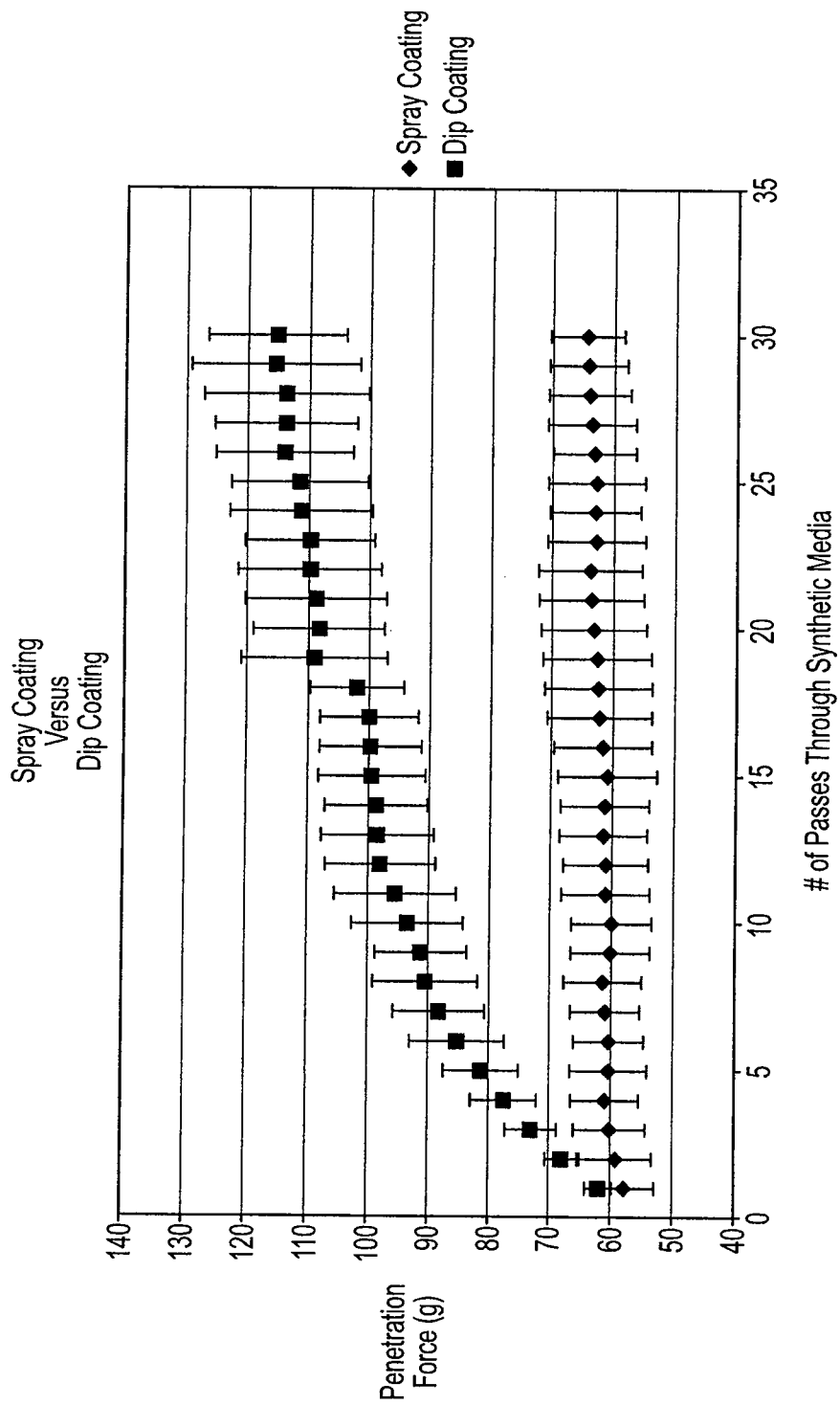

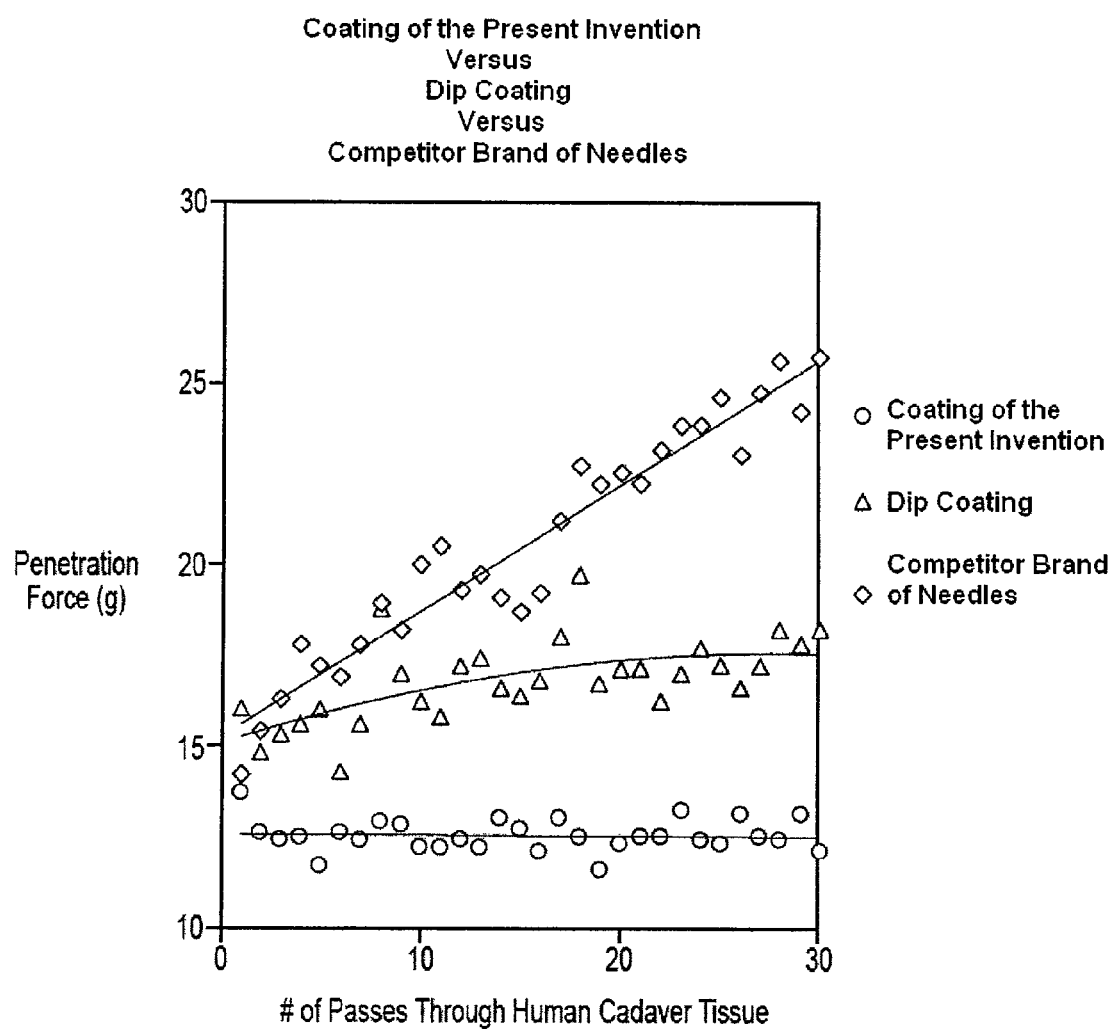

SURGICAL NEEDLE COATINGS AND METHODS

CROSS REFERENCE TO RELATED APPLICATIONS

This application is a divisional of U.S. patent application Ser. No. 12/858,489 filed on Aug. 18, 2010 and entitled "Surgical Needle Coatings and Methods," which is a continuation-in-part of U.S. patent application Ser. No. 12/614,669, filed on Nov. 9, 2009 and entitled "Surgical Needle Coatings and Methods," all of which are hereby incorporated by reference in their entireties.

FIELD OF THE INVENTION

The present invention relates to coated medical devices and methods for manufacturing the same.

BACKGROUND OF THE INVENTION

Coated medical devices which repeatedly come into contact with bodily tissue, such as surgical needles, are required to be lubricious, yet durable enough to withstand multiple contacts with tissue. However, lubricity is often sacrificed at the expense of making a more durable coating that adheres well to medical devices. There are many coating materials that are extremely lubricious, but either do not adhere well to the desired substrates or easily wear off the substrate during use. Likewise, many extremely durable coatings exist, but these coatings are not considered lubricious. Various attempts have been made to find coating compositions and/or a method of applying coating compositions that can provide durability and lubricity simultaneously. Accordingly, the present invention solves this problem by providing coating compositions and methods of application, which provide both durability and lubricity, as well as decreased manufacturing time.

SUMMARY OF THE INVENTION

While any medical device can be provided with regard to the examples described herein, in one exemplary embodiment, a surgical needle is provided having an elongate body with a tissue-penetrating end and a suture attachment end. The surgical needle can have a base coating disposed on an exterior surface of the elongate body and a top coating that differs from the base coating. The top coating can include a lubricious silicone disposed on the base coating such that the base coating bonds with the top coating and enhances the durability of the top coating.

In one embodiment, the surgical needle can be passed through tissue, and a force required to penetrate the tissue-penetrating end of the elongate body through tissue can remain substantially constant after multiple passes through tissue (e.g., at least about twenty times and more preferably, at least about thirty times). The surgical needle can be formed from any suitable material known in the art including, but not limited to, tungsten-rhenium alloys, refractory alloys, stainless steels, nitinol, and tantalum.

In some embodiments, a primer coating can be disposed between the exterior surface of the elongate body and the base coating and can bond with the exterior surface of the elongate body and the base coating. The primer, base, and top coatings can be formed from any suitable composition known in the art, but in one exemplary embodiment, the primer coating can be silicone-based, the base coating can include a vinyl functionalized organopolysiloxane, and the top coating can include a hydroxyl terminated polydimethylsiloxane and a methyl-hydrogen siloxane.

In another embodiment, a surgical needle is provided and can include an elongate body formed from a tungsten-rhenium alloy and having a tissue-penetrating tip. A primer coat can be disposed on an exterior surface of the elongate body and can covalently bond with reactive functional groups on the exterior surface of the elongate body. Any number of coatings can be disposed over the primer coat, for example, a base coat can be disposed over the primer coat and a top coat can be disposed over the base coat. In some embodiments, the base coat can bond with the primer coat, and the top coat can bond with the base coat. Bonding can include, for example, at least one or both of covalent bonding and cross-linking.

In other aspects, a surgical needle is provided and can include an elongate member having a tissue-penetrating tip and a suture attachment portion. The elongate member can have, for example, base and top coatings. The coatings can be formed from any suitable composition, but in one embodiment, the base coating can include a vinyl functionalized organopolysiloxane and a hydrofluoroether solvent, and the top coating can include a polydimethylsiloxane and a hydrofluoroether solvent.

Various coating methods known in the art can be used to apply the coatings, for example, the base and top coatings can be spray-coated onto the elongate member. In some embodiments, the elongate member can further include a primer coating formed from a coating mixture that can include a silicone resin and a solvent. The elongate member can be formed of any suitable material known in the art including, but not limited to, a tungsten-rhenium alloy. The primer coating can be disposed on and can at least partially covalently bond with the elongate member. The base coating can be disposed on the primer coating, and the top coating can be disposed on the base coating. The coatings can have any thickness sufficiently effective for a particular application.

Methods for coating a surgical needle are also provided, and in one embodiment, a method for coating a surgical needle can include providing a surgical needle having a tissue-penetrating end and a suture attachment end, applying a base coating to a surface of the surgical needle, and applying a top coating that differs from the base coating onto the base coating. The base coating can bond with the top coating and can enhance the durability of the top coating.

Many curing and processing methods can be applied to the coatings and in one embodiment, after applying the base coating and prior to applying the top coating, the method can include curing the base coating. In addition, the method can further include, prior to applying a base coating and applying a top coating, preparing the base coating from a mixture that can include a vinyl functionalized organopolysiloxane and a hydrofluoroether solvent, and preparing the top coating from a mixture that can include a polydimethylsiloxane and a hydrofluoroether solvent.

In some embodiments, prior to applying the base coating, the method can include applying a primer coating onto the surface of the surgical needle such that the base coating can be applied onto the primer coating. The surgical needle can be formed of any biocompatible material known in the art including, but not limited to, tungsten-rhenium alloys, refractory alloys, stainless steels, nitinol, and tantalum. In one embodiment, the primer coating can at least partially covalently bond with a surface of a needle made from a tungsten-rhenium alloy.

In other aspects, a method for coating a surgical needle can include providing a surgical needle having a tissue-penetrating end and a suture attachment end, positioning the surgical needle between first and second nozzles, the first and second nozzles being opposed to and facing one another, and activating the first and second nozzles to spray a base coating onto a surface of the surgical needle. The method can further include positioning the surgical needle between third and fourth nozzles, the third and fourth nozzles being opposed to and facing one another, and activating the third and fourth nozzles to spray a top coating on at least a portion of the base coating, the top coating differing from the base coating.

In some embodiments, each nozzle can dispense a rotating spray of coating particles that swirl around the surgical needle to coat the surgical needle. The method can further include adjusting an angle of a fluted tip within each nozzle to control a pitch of the rotating spray dispensed by the nozzle and moving the surgical needle and the first and second nozzles relative to each other at a relative speed in the range of about 1 inches per second to about 15 inches per second, and more preferably in the range of about 3 inches per second to about 15 inches per second, while the nozzles are activated to spray a coating. The first and second nozzles can be positioned at an angle less than 180° relative to one another in a horizontal plane. The base and top coatings can have any thickness sufficient to effectively provide the desired characteristics.

In other embodiments, a method for coating a surgical needle can include providing a surgical needle formed from a metal alloy, applying a primer coat to the surgical needle, the primer coat at least partially covalently bonding with the metal alloy, applying a base coat onto the primer coat, the base coat bonding with the primer coat, and applying a top coat onto the base coat, the top coat bonding with the base coat. The base coat and the top coat can be applied by spray-coating. The coatings can have any suitable composition known in the art, for example, the primer coat can include a silicone, the base coat can include a vinyl functionalized organopolysiloxane, and the top coat can include a methyl terminated polydimethylsiloxane.

The invention will be more fully understood from the following detailed description taken in conjunction with the accompanying drawings, in which:

BRIEF DESCRIPTION OF THE DRAWINGS

FIG. 2 is a side view of a carrier strip with surgical needles attached thereto for transporting the surgical needles;

FIG. 3B is a perspective view of another exemplary embodiment of a swirl coating machine for coating suspended surgical needles;

FIG. 5 is a graphical representation comparing the force required to pass primed and unprimed surgical needles through synthetic media;

FIG. 6 is graphical representation comparing the force required to pass surgical needles that are swirl coated through synthetic media versus surgical needles that are dip coated;

FIG. 7 is a graphical representation comparing forces associated with two different coating compositions and application methods;

FIG. 8 is a graphical representation comparing the force required to pass surgical needles that are swirl coated through synthetic media versus surgical needles that are dip coated; and FIG. 9 is a graphical representation comparing the forces associated with passing three different coating compositions and application methods through human cadaver tissue.

DETAILED DESCRIPTION OF THE INVENTION

Figure 1:
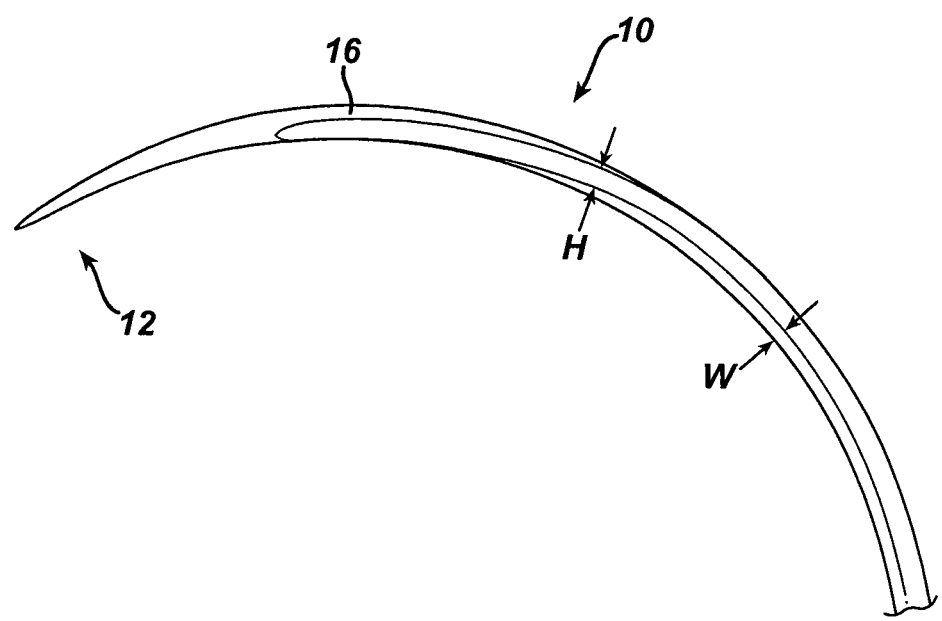
FIG. 1 is a perspective view of one exemplary embodiment of a surgical needle.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides improved medical devices for use in surgical procedures and methods for manufacturing improved medical devices. In some embodiments, the improved medical devices can include improved surgical needles that are capable of being repeatedly passed through tissue with ease of penetration. More particularly, the improved surgical needles can be manufactured with two or more different coatings that provide the surgical needles with both durability and lubricity for ease of repeated and successive passes through tissue. Improved methods for manufacturing the surgical needles and for providing and applying coatings to the surgical needles are also provided.

While many types of medical devices and surgical needles are contemplated, in one embodiment, a biocompatible surgical needle is provided having two or more different coatings applied successively thereto. A base coating can be applied to the needle to provide durability for a different top coating that is applied to provide lubrication. The base coating can also be lubricious to enhance the lubricity of the top coating. In some embodiments, the base and top coatings interact, for example, by cross-linking or other bonding mechanism, so that the base coating retains the top coating on the surgical needle. In this way, the base coating can assist in preventing the top coating from wearing and/or rubbing off after repeated passes through tissue. In other embodiments, each of the base coating and/or the top coating can cross-link with itself. The interaction between the durable base coating and the lubricious top coating assists in maintaining lubrication of the surgical needle so that it can consistently and repeatedly be passed through tissue with minimal force required.

Any number of coatings can be applied to the surgical needle depending on the surgical application and the composition of the surgical needle. For example, in another embodiment a primer coating can be applied to the surgical needle before the base and top coatings are applied. The primer coating can be different from the base and top coatings and it can bond with a surface of the surgical needle to provide an appropriate and secure surface on which to apply the base coating. In turn, the base coating can bond to the primer coating such that the primer coating securely retains the base coating on the surgical needle.

Improved methods for applying the coatings to various medical devices, such as surgical needles, are also provided.

In some embodiments, a surgical needle can be spray coated with one or more coatings to provide the surgical needle with a uniform distribution thereof. For example, a spray coating machine having two spray nozzles directed toward one another can be provided for successively applying each coating. One or more surgical needles can be passed between the two spray nozzles as they are spraying a coating. Such a configuration allows for uniform distribution of the coating on the surgical needle and minimizes the risk of pooling and/or dripping of the coating. Multiple coatings can be applied using this method, and prior to and/or after application of each coating, the surgical needle can be cured for a sufficient period of time effective to set and bond the coating(s). As will be discussed in more detail below, novel combinations of solvents and coating materials can allow for substantially reduced cure times when compared with techniques known in the art.

Exemplary surgical needles of the type contemplated herein can generally be used for any surgical procedures now known or yet to be developed. The surgical needles can be capable of penetrating and passing through any type of tissue, including any type of mammalian tissue including soft and hard tissues and tissues that have been calcified, and can be used to apply sutures to close an incision or wound, pass suture or other material through tissue, and/or simply create an opening in tissue. A person skilled in the art will appreciate the variety of uses for the surgical needles described herein.

Exemplary surgical needles can generally include an elongate member with a tissue penetrating tip on a distal end thereof for penetrating through tissue. The tissue penetrating tip can be pointed and can be as sharp or as dull as required for a particular surgical procedure. In some embodiments, the surgical needle can also include a suture attachment portion disposed on a proximal end of the elongate member for receiving and retaining suture. The surgical needle can have any geometry known in the art, including straight, taper point, taper cut, cutting edge, bayonet-shaped, curved, circular, etc. In addition, the surgical needle can have any cross-section including, but not limited to, round body, rectangular body, square body, ovular body, and I-beam. A person skilled in the art will appreciate the various combinations of shapes and cross-sections possible for a given needle.

In the manufacturing process, surgical needles can have a straightened and/or hook-shaped grasping portion to assist in applying coatings thereto. A conveyer mechanism and/or carrier strip for manufacturing a needle and/or moving a needle through a coating machine and/or curing mechanism can retain the needle for manufacturing, coating, and curing by attaching to the grasping portion. An exemplary carrier strip 20 for use with surgical needles 24 is illustrated in FIG. 2. The carrier strip 20 includes various latches 22 for retaining the curved surgical needles 24 thereon. This allows the surgical needles 24 to be moved using a conveyor style mechanism during the coating and/or curing process.

One exemplary embodiment of a surgical needle is illustrated in FIG. 1. As shown, a surgical needle 10 is provided having a curved elongate body 16 with a tissue penetrating tip 12 formed on a distal end thereof. The tip 12 has a circular cross-section and terminates in a sharp point for penetrating tissue. The curved elongate body 16 extends between the tip 12 and a suture attachment portion (not shown) and is in the form of an arc with a flattened, rectangular cross-section. While the surgical needle 10 can have any relative dimensions as needed, in the illustrated embodiment, a width W of the needle 10 is on the order of a height H of the needle 10. A suture attachment portion can have any form as needed for receiving and retaining suture.

Exemplary surgical needles can be formed of any suitable, biocompatible material known in the art. In some embodiments, a surgical needle can be made of a metallic alloy, including, but not limited to, titanium, stainless steels such as 420 stainless steel, 455 stainless steel, ETHALLOY® Needle Alloy, and 302 stainless steel, refractory alloys, nitinol, tantalum, as well as various other materials and alloys known in the art. In other embodiments, surgical needles can be made from a tungsten-rhenium alloy. Use of tungsten-rhenium alloy in making surgical needles can give the needles greater stiffness, strength, and ductility than the use of some other materials. Increased stiffness and strength properties allow the needle to be resistant to elastic deformation and to thus resist bending and springing when pushed through tough tissue, for example, calcified tissue. Increased ductility prevents the needle from breaking when bent or curved by a surgeon. Any of the needle alloy compositions can contain some percentage of any one or more of nickel, cobalt, chromium, molybdenum, tungsten, rhenium, niobium, etc. Exemplary needles and methods for manufacturing needles and carrier strips can be found in U.S. Pat. No. 6,018,860, entitled "Process for Manufacturing Drilled Taper Point Surgical Needles," which is hereby incorporated by reference in its entirety.

In general, two or more different coatings can be used to provide exemplary surgical needles with a durable lubricious surface for repeated passes through tissue. In one exemplary embodiment, a base coat can be used to coat an external surface of a surgical needle to provide durability to a top coat that is applied onto the base coat and that provides lubrication. The base coat preferably bonds with the top coat and thus prevents and/or lessens wear associated with repeated penetrations and passes through tissue. In some embodiments, a primer coat can optionally be applied prior to the base coat. The primer coat can bond with the surface of the surgical needle to provide a bonding surface for the base coat. The primer coat can add additional durability against wear for the base coat and top coat.

In some embodiments, the base coat can include a silicone based composition characterized as a vinyl functionalized organopolysiloxane. The base coat solution includes a vinyl functionalized organopolysiloxane, polymethylhydrogen siloxane fluid cross-linking agent, and optionally a catalyst such as a conventional metal catalyst such as platinum or tin. The organopolysiloxane base polymer can be, for example, Momentive® Product Code No. MSC2631 silicone manufactured by Momentive® Performance Materials of Waterford, N.Y. Further information on the MSC2631 composition is available from the manufacturer's MSDS.

The base coat can be prepared using a solvent, for example, a hydrofluoroether ("HFE") (e.g., HFE 72-DE solvent manufactured by 3M® of St. Paul, Minn.). The HFE solvent acts as a carrier for the silicone composition. It evaporates quickly from a composition under ambient conditions to limit migration of other substances in the composition and thus drastically reduces cure time of the composition. In addition, the HFE solvent leaves no residue after evaporation. It complies with health and safety regulations and is environmentally friendly. As will be appreciated by those skilled in the art, any suitable solvent can be used including, but not limited to, HFE, xylene, heptane, IsoPar K (Dow Corning), napthalene, toluene, and hydrofluorocarbons.

Additionally, a catalyst and a cross-linker can be added to the base coat. For example, Momentive® Product Code No. SS8010 platinum catalyst ("catalyst") and Momentive® Product Code No. SS4300 cross-linker ("cross-linker"), both manufactured by Momentive® Performance Materials of Waterford, N.Y., can be added during the preparation of the base coat to act as a cross-linker and catalyst. As will be appreciated by those skilled in the art, any suitable catalysts and cross-linkers can be used including, but not limited to, other cross-linkers containing a silicon-hydrogen moiety. Other catalysts may include conventional metal catalysts such as tin.

In preparing an exemplary base coat, 27.57 wt. % of the base silicone polymer, for example, a vinyl-functionalized organopolysiloxane, can be combined with 72.27 wt. % of the HFE solvent and mixed and/or agitated for an appropriate period of time, for example, for about five minutes. The catalyst can then be added to the mixture at 0.02 wt. % and the cross-linker can be added at 0.14 wt. %. The mixture can be agitated for another few minutes to ensure homogeneity, for example, about one to two more minutes. For an exemplary 48.43 g base coat sample, 13.35 g of the base silicone polymer can be combined with 35.00 g of the HFE solvent, 0.012 g of the catalyst, and 0.068 g of the cross-linker.

A top coat can be applied to a surgical needle. In some embodiments, the top coat can include a silicone based composition characterized as a hydroxyl terminated polydimethylsiloxane. The hydroxyl terminated polydimethylsiloxane generally includes dimethyl siloxane-hydroxy terminated, methylhydrogen siloxane, and trace amounts of several other siloxanes. The hydroxyl terminated polydimethylsiloxane can be, for example, NuSil® Technologies Silicone Product No. MED4162 manufactured by NuSil® Technologies of Carpentaria, Calif., which is a dispersion that contains 30% solids silicone in a 70% xylene solvent carrier.

The top coat can be prepared using a solvent, for example, the HFE solvent or any other compatible volatile-solvent. In preparing an exemplary top coat, 26 wt. % of the top silicone polymer can be combined with 74 wt. % of the HFE solvent. For example, for a 50 g top coat sample, 13.00 g of the top silicone polymer can be combined with 37.00 g of the HFE solvent.

In some embodiments, a primer coat can optionally be applied to a surgical device prior to applying the base coat. The primer coat can have any formulation capable of bonding to a surgical needle and capable of providing an appropriate substrate for applying a base coat. In one embodiment, the primer coat can be formed of, for example, polyalkylsiloxane and tetraethyl silicate. A polyalkylsiloxane and tetraethyl silicate primer coat can be formulated for coating difficult-to-bond substrates such as, for example, tungsten-rhenium alloys.

One example of a polyalkylsiloxane and tetraethyl silicate primer coat is Momentive® Product No. SS4044P ("SS4044P primer") manufactured by Momentive® Performance Materials of Waterford, N.Y. The SS4044P primer can include Momentive®) 10-30 wt. % of acetone, 1-5 wt. % of butanol, 10-30 wt. % of xylene isomers mixture, 5-10 wt. % of ethylbenzene, 10-30 wt. % of 2-propanol, 1-5 wt. % of tetraethyl silicate, and 10-30 wt. % of polyalkylsiloxane. Further information on the SS4044P primer composition is available from the manufacturer's MSDS.

In general, as noted above, the primer coat can covalently bond to the surgical needle to provide a substrate on which to apply other coatings. The base coat can be applied on top of the primer coat. As the top coat is applied over the base coat, the base coat will bond with the top coat to provide durability to the top coat. In essence, the bonding between the primer coat and the surgical needle anchors the other two coats to the needle surface. The bonding of the base coat to both the primer coat and the top coat anchors the top coat to the primer coat, and thus to the surgical needle surface, giving the top coat extended durability.

The coatings can generally be applied at any thickness as needed. The thickness of the individual coatings and the combined coatings should be sufficient to provide the desired characteristics. For example, the primer coat can be applied to have a thickness in the range of about 0.01 µm to about 1 µm. The base coat and the top coat can be applied with a thickness in the range of about 1 µm to about 7 µm. In an exemplary embodiment, the top coat can have a thickness that is at least about 50% less than a thickness of the base coat. A person skilled in the art will appreciate that the thicknesses of the coatings can vary depending on a particular application.

There are many methods and systems contemplated herein that can be used to provide coated surgical needles or other medical devices. In general, a medical device such as a surgical needle can be produced from a desired material and prepared for coating, as described in more detail below. One or more coatings can be applied to the surgical needle to provide durability and lubricity during use. Before, during, and/or after application of any one of the coatings, the surgical needle can be cured for a sufficient amount of time effective to remove solvents in the coatings and/or to set, cross-link, and/or bond a coating.

Any process known in the art can be used to coat various medical devices with one or more of a base coat, top coat, and/or primer coat including, but not limited to, dipping, spraying, wiping, brushing, total immersion, gravity feed, etc. For example, surgical needles can be dip coated in a number of traditional ways. If needles are being processed manually, the needles can be hand dipped or totally submersed in a coating. In a more automated process, coating solutions can be applied using a weir type circulating system in which surgical needles pass through the solution in an automatic fashion, either by robot or handling system. Dip techniques generally rely on surface tension for adhesion of the coating and wetting characteristics of the coating with relation to the substrate for continuity.

In one embodiment, one or more coatings can be applied to a surgical needle by spraying using, for example, ultrasonic and/or gas conformal coating spray nozzle systems and/or swirl coating systems. Ultrasonic and gas spray nozzles transmit energy to a liquid in an amount sufficient to atomize the liquid and form a spray of droplets. The spray of droplets can be applied to a medical device using a swirl process in which the droplets are swirled around the medical device in order to coat the substrate. Application of a coating using the swirl process can ensure a more even distribution of the coating to a surgical device while preventing excess collection of the coating that may result in drips, undesired pooling, droplets, and/or unevenness. Spraying also allows for precise control and adjustment of coating thickness. A particular coating can be applied to leave only a thin film on a surface or it can be applied to provide different thicknesses.

Different types and sizes of spray nozzles can be used depending on the specific coating compositions and the desired attributes of the spray stream generated. Spray nozzles can be designed to operate at specific frequencies and/or air pressures as needed and the desired power level for operating the nozzles can depend on various factors including the size and design of the nozzle, the viscosity of the composition being used, the volatility of components in the composition being used, etc. Both ultrasonic and fluid spray nozzles are available commercially.

Figure 3A:
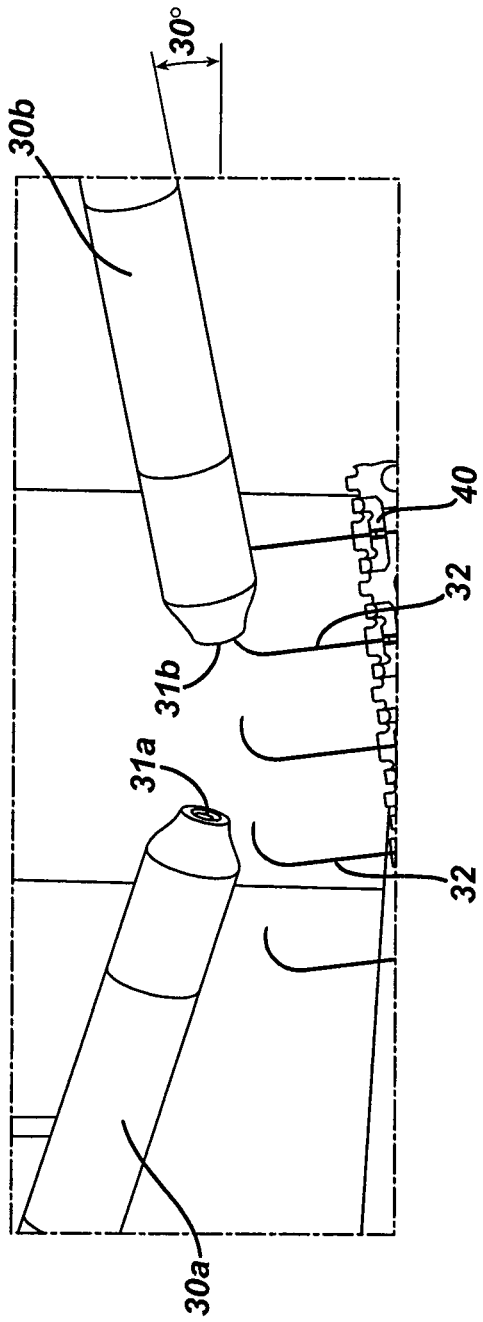
FIG. 3A is a perspective view of one exemplary embodiment of a swirl coating machine for swirl coating surgical needles.

In one embodiment, such as those illustrated in FIGS. 3A and 3B, opposed spray nozzles 30a, 30b are provided for applying a swirl coating to exemplary surgical needles 32. The opposed spray nozzles 30a, 30b can each be coupled to canisters holding a particular coating to be applied and can deliver the coating through discharge openings 31a, 31b. Each coating to be applied by the swirl process can be applied using different pairs of opposed spray nozzles 30a, 30b. Thus, in some embodiments, multiple sets of spray nozzles can be used to apply multiple coatings. Each spray nozzle 30a, 30b can have a fluted tip (not shown) for delivering the coating. An angle of the fluted tip, relative to a horizontal plane through which the needles extend perpendicular to, can be adjusted to focus the band of spray to optimize coating. As will be appreciated in the art, any angle can be used as needed to deliver a particular coating. In addition, different coatings may require delivery from a fluted tip with a different angle.

The opposed pair of spray nozzles 30a, 30b can extend from a positioner (not shown) capable of adjusting and maneuvering the spray nozzles 30a, 30b in three dimensions. The opposed spray nozzles 30a, 30b can be positioned in any way relative to each other as needed for a particular application and can generally be symmetrically opposed to one another. In the illustrated embodiment, the spray nozzles 30a, 30b are positioned at approximately a 30 degree angle, as shown in FIGS. 3A-3B, relative to a horizontal surface. Horizontally, the nozzles 30a, 30b can be directly opposed, e.g., offset by 180 degrees. Preferably, however, the nozzles 30a, 30b can be horizontally offset relative to each other by an amount less than 180 degrees to prevent neutralization and to prevent overspray from collecting on the needles. The positioning of the opposed nozzles 30a, 30b can be optimized to provide the most complete coating of a surgical needle.

In general, the swirl coating can be applied during relative movement between the needles 32 and the nozzles 30a, 30b. In some embodiments, one or more needles 32 can remain stationary while the nozzles 30a, 30b move relative to the needles 32 while spraying the coating. In other embodiments, a carrier strip, such as the carrier strip 20 shown in FIG. 2, or a carrier strip 40 shown in FIGS. 3A and 3B, can move a plurality of surgical needles 32 relative to the opposed spray nozzles 30a, 30b while the nozzles 30a, 30b remain stationary. In other embodiments, both the carrier strip 40 and the nozzles 30a, 30b can move relative to one another. The carrier strip 40 can be mounted below the nozzles 30a, 30b as shown in FIG. 3A, or the carrier strip 40 can be mounted above the nozzles 30a, 30b as shown in FIG. 3B.

The movement speed of the carrier strip 40 and/or the nozzles 30a, 30b can be controlled so that the spray nozzles 30a, 30b provide optimal coverage and coating of the needles 32. For example, relative movement speed between the needles 32 and the nozzles 30a, 30b can be in the range of about 1 to about 15 inches per second. Optimally, the relative movement speed can be in the range of about 3 inches per second to about 5 inches per second. Shields may be optionally disposed between the nozzle discharge openings 31a, 31b and the proximal portion of the needle.

There are many mechanisms known in the art for curing, hardening, and/or setting a coating on a surgical device such a surgical needle. Curing can also cause evaporation of any solvent used in making the coating. Curing can generally be accomplished through exposure of a coated surgical needle to some form of temperature increase and/or humidity change for a predetermined period of time. For example, the coated needles can be placed in a furnace or oven, a hotbox, a humidification chamber, and/or an infrared chamber, among other forms known in the art. Curing times can range from "flash" curing of only a few seconds to times longer than twenty-four hours.

During the curing process, the temperature and/or humidity can be maintained at a single value for the entire time and/or it can be increased or decreased as needed over time. Temperature can be monitored and adjusted using, for example, a thermocouple and a potentiometer to control power to heating elements. The potentiometer can be preconfigured so that temperature measurements made by the thermocouple at periodic increments along a length of the heating system are maintained at or between a specified temperature range. In other embodiments, temperature can be controlled using a feedback loop where temperature measurements that correlate to temperatures where surgical needles will pass are fed back to a power supply that continuously adjusts power delivered to the heated filaments to maintain a desired temperature range. A humidity monitor can be used to monitor and adjust humidity. In some embodiments, each coating can be cured after application thereof to the surgical needle. In other embodiments, all coatings can be applied before initiating the curing process.

In one embodiment, an infrared emitter can be used to effect curing of a coating. Infrared emitters are available commercially from Heraeus® Noblelight, for example, Model SKL200-800. The actual emitters can include, for example, eight foot long thin heated filaments embedded within a reflective channel used to focus and contain the heat. The infrared heating system can be oriented so that the channel's opening is facing down. Surgical needles to be cured in the infrared heating system can be held vertically and passed between two concave reflective walls of the channel at about, for example, ¼ inch from the heated filaments. Needles can be held on a carrier strip as they traverse the channel at a speed in the range of about 3 inches per second to about 5 inches per second, although any speed can be used.

Figure 4:
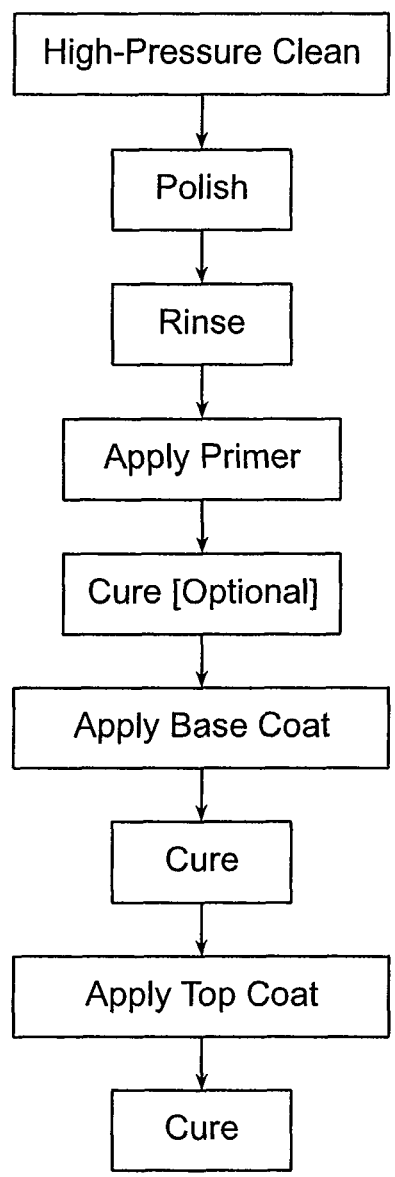
FIG. 4 is a flowchart of one exemplary method for manufacturing and coating surgical needles.

While many methods for providing durable lubricious coatings on surgical needles are contemplated, a flow chart of an embodiment of one particular method is illustrated in FIG. 4. As shown, the method can generally include manufacturing the surgical needles, preparing the surface of the needles for receiving a coating, coating the needles with a primer coat, base coat, and/or top coat, and curing the coatings. A person skilled in the art will appreciate the variations and additions that can be included in such a method.

In manufacturing the surgical needles, raw wire of a suitable composition can be unspooled and cut into blanks for shaping. While any size blanks can be used depending on the size of the needle desired, in one embodiment, the wire can be cut into two inch blanks. Once cut, the blanks can be attached to a metal carrier strip, such as that illustrated in FIG. 2. The blanks can be secured and shaped into their preferred needle form by any methods known in the art, including forming, grinding, curving, etc.

Needles that are appropriately shaped can be cleaned to remove contaminates and to prepare the surface for receiving a coating. For example, the needles can be exposed to high pressure nozzles that release water at high temperature and pressure. In other embodiments, the needles can be baked to high temperatures to release any contaminates. Once the needles have been cleaned, they can be electropolished for any amount of time necessary. The needles can be immersed in the electropolish bath (e.g., sodium hydroxide, phosphoric acid, etc.) and subjected to direct current to remove ions at a controlled rate. Once complete, the needles can be rinsed successive times, for example, two times, in de-ionized water baths.

In some embodiments, a primer coat, such as the SS4044P primer described above, can be applied to the newly manufactured and cleaned surgical needles. The primer coating can be used, for example, when the needle is a tungsten-rhenium alloy. The primer can be applied using any method known in the art including dipping or spraying, but in one embodiment, the primer is applied to the surgical needles by dipping. Using a grasper or carrier strip, the needles can be dipped into the primer at room temperature for one to two seconds to effect complete coverage thereof. A person skilled in the art will appreciate that primers can be applied at any temperature and for any length of time as appropriate for a particular primer. Reactive functional groups in the primer can react with the functional hydroxide groups in the surface of the surgical needles and covalently bond thereto. In some embodiments, after the primer coating has been applied, the surgical needle can be flash cured for about 20 seconds at an appropriate temperature, for example, about 200 degrees Celsius. Once cured, the primer can create a boundary between the surface of the surgical needle and any later applied coatings.

A base coat, such as the Momentive® base coat described above, can be applied to the external surface of the surgical needle, and over a primer if utilized, for example, the SS4044P primer. Any application method known in the art can be used, but in one embodiment, the surgical needle is sprayed or swirl coated with the base coat using opposed spray nozzles. For example, the surgical needle can be passed between first and second opposed spray nozzles to be coated. Application of the base coat using the spray or swirl coating ensures an evenly distributed layer of the base coat on the needle or over the primer, if utilized. As the base coat is applied, the solvent, for example, the HFE solvent, can rapidly evaporate to leave a thin layer of evenly distributed silicone on the needle surface. In some embodiments, the base coat can be cured onto the surface by exposure to an "in-line" infrared heating system. The base coat can be exposed to a number of different wavelengths of infrared light and cured.

The coated medical device of the invention may also have a top coat applied over the base coat, more preferably after the base coat is partially cured. For example, the NuSil® top coat described above can be applied over the Momentive® base coat. Any application method known in the art can be used, but in one embodiment, the surgical needle can be sprayed or swirl coated with the top coat using opposed spray nozzles. For example, the surgical needle can be passed between third and fourth opposed spray nozzles to be coated. Application of the top coat using the spraying or swirl coating technique ensures an evenly distributed layer of the top coat over the base coat. As the top coat is applied, the solvent, for example, the HFE solvent, can rapidly evaporate to leave a thin layer of evenly distributed top coat over the base coat. In some embodiments, after application of the top coat, the top coat can be flashed cured to drive off any excess solvent. The needles can be passed through, for example, a hot box or other heated curing system, for any time and at any temperature necessary to accomplish evaporation of the solvent. In one embodiment, the top coat can be flashed cured in an infrared heater for approximately 20 seconds at a temperature in the range of about 165 degrees Celsius to about 200 degrees Celsius.

Following application of the top coat, the surgical needles can be optionally re-spooled. In some embodiments, the coated surgical needles can be exposed to a final curing process. For example, the re-spooled needles can be placed inside a convection oven and cured at a temperature and time sufficient to further cure the coating. In one embodiment, the surgical needles can be cured in the convection oven for approximately four hours at about 165 degrees Celsius. In other embodiments, the final cure can be performed at a temperature of about 80 degrees Celsius for approximately three hours.

The cure times for the exemplary coatings and methods described herein are extremely beneficial in that they are significantly less than cure times for previous coatings and methods known in the art. Previous coatings and methods could require curing of the surgical needles for up to 72 hours plus processing and coating time. The currently described exemplary coatings and methods can reduced the total curing time to less than about 4 hours and possibly less than about 15 minutes, providing a significant increase in efficiency for manufacturing of the needles.

The use of two coatings as described above results in surgical needles that exhibit reduced and/or generally constant tissue penetration force compared with standard surgical needles after an equivalent number of passes through tissue. Thus, both the lubricity of the needle as well as the durability of the coating is improved. This effect is believed to result for a number of reasons. For example, application of the base and top coats using a swirl coating process provides an even distribution of the coatings over the substrate. This is most clearly represented in FIG. 6, which will be described in more detail below. In addition, the compositions of the coatings in combination with the methods of application and curing can result in significantly decreased average force required to repeatedly pass the needle through synthetic media, as shown in FIG. 7, which will also be described in more detail below.

The use of the optional primer coating can also be advantageous. A primer coating can be capable of chemically bonding to the needle surface to provide a bonding substrate for the lubricious silicone coatings to adhere to, resulting in increased durability of the base and top coatings. For example, FIG. 5 illustrates the force required to pass a needle through synthetic media in relation to the number of passes through synthetic media. As shown, needles without primer have a drastic rise in the force required after thirty passes when compared with primed needles of identical material and configuration, which tend to maintain a fairly constant force up to at least thirty passes through synthetic media. More detail will be presented in the examples described below.

Coating performance for medical devices can generally be tested with a variety of conventional tests. In the case of surgical needles, coating performance and integrity is evaluated using a penetration test device. A portion of a coated surgical needle is held using a holding device, and the coated needle is then partially passed through a synthetic or natural penetratable material some number of times. The material is typically a type of polymer or synthetic leather, for example, Permair, Rubber-Cal, Monmouth rubber, Porvair, etc. The needle can be passed through the penetratable material for about one to about twenty times, between about one to about twenty-five times, and most preferably between about one to about thirty times. The needle is then retracted from the media. The maximum force is recorded for each pass and is used as a measure of the coating performance. Various attributes of coating performance can be tested using these techniques.

EXAMPLES

The following experiments were conducted to examine the effects of varying the needle coating materials and methods. For each test, the needles were passed through Monmouth Duraflex MR40 NBR rubber membrane ("Monmouth rubber"), which serves to simulate flesh, or human cadaver tissue. In the following non-limiting examples, from 4 to 10 needles were used and individually passed through the penetration membrane thirty times each. The maximum force in grams was recorded for each pass and used as a measure of coating performance.

The surgical needles were mounted in a rotating stage to fix the needle in a position perpendicular to the penetration membrane surface and oriented on its radial profile with the axis of rotation on the same plane as the plane of the penetration membrane. The needle was rotated into the penetration membrane, which was mounted on top of the load cell. The maximum amount of vertical force was recorded as the needle was pushed through the penetration membrane.

for ninety minutes at ambient atmosphere. The needles were then allowed to cool at ambient temperature outside of the oven.

A top coating composition was prepared using 26 wt. % of NuSil® MED4162 with 74 wt. % HFE-72DE solvent. The five needles were then each hand dipped into the top coating composition. The needles were then heated to 220 degrees Celsius in a convection oven and cured for four hours at ambient atmosphere. The needles were allowed to cool at ambient temperature outside of the oven.

Once cured, the five needles were each passed through the penetration membrane thirty times and the penetration force in grams was recorded as shown in Table 1 below.

TABLE 1

| Experiment | Needle | Pass --> Penetration (g) | | | | | | | | | | | | | | |
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| A | 1 | 39 | 38 | 41 | 40 | 42 | 47 | 42 | 46 | 43 | 47 | 47 | 46 | 48 | 49 | 52 |
| | 2 | 40 | 42 | 45 | 46 | 46 | 49 | 50 | 55 | 51 | 51 | 56 | 53 | 56 | 57 | 63 |
| | 3 | 40 | 41 | 41 | 47 | 45 | 46 | 49 | 51 | 51 | 45 | 50 | 52 | 52 | 57 | 54 |
| | 4 | 34 | 34 | 36 | 36 | 36 | 36 | 38 | 37 | 40 | 39 | 42 | 41 | 44 | 43 | 45 |
| | 5 | 38 | 38 | 38 | 40 | 42 | 44 | 47 | 45 | 48 | 48 | 46 | 50 | 49 | 52 | 51 |
| | St Dev | 2.5 | 3.1 | 3.4 | 4.6 | 3.9 | 5.0 | 5.1 | 6.8 | 4.9 | 4.5 | 5.2 | 4.9 | 4.5 | 5.9 | 6.5 |
| | Avg | 38.2 | 38.6 | 40.2 | 41.8 | 42.2 | 44.4 | 45.2 | 46.8 | 46.6 | 46.0 | 48.2 | 48.4 | 49.8 | 51.6 | 53.0 |
| Experiment | Needle | 16 | 17 | 18 | 19 | 20 | 21 | 22 | 23 | 24 | 25 | 26 | 27 | 28 | 29 | 30 |
| A | 1 | 53 | 45 | 53 | 57 | 48 | 56 | 53 | 55 | 56 | 54 | 57 | 57 | 57 | 60 | 61 |
| | 2 | 59 | 54 | 64 | 62 | 65 | 69 | 62 | 66 | 68 | 68 | 71 | 75 | 73 | 72 | 69 |
| | 3 | 56 | 55 | 58 | 56 | 57 | 60 | 61 | 59 | 62 | 61 | 61 | 62 | 60 | 64 | 62 |
| | 4 | 45 | 45 | 46 | 48 | 49 | 48 | 49 | 51 | 53 | 53 | 50 | 53 | 52 | 56 | 53 |
| | 5 | 51 | 51 | 52 | 50 | 54 | 51 | 56 | 52 | 57 | 59 | 53 | 58 | 61 | 58 | 58 |
| | St Dev | 5.3 | 4.8 | 6.8 | 5.6 | 6.9 | 8.2 | 5.4 | 6.1 | 5.9 | 6.0 | 8.2 | 8.5 | 7.8 | 6.3 | 5.9 |
| | Avg | 52.8 | 50.0 | 54.6 | 54.6 | 54.6 | 56.8 | 56.2 | 56.6 | 59.2 | 59.0 | 58.4 | 61.0 | 60.6 | 62.0 | 60.6 |

The following non-limiting examples serve to further illustrate the application:

Example 1

The following tests were performed to examine the effect coating methods have on the force required to pass a needle through Monmouth rubber synthetic media. The performance of needles that were dip coated was compared with the performance of needles that were spray/swirl coated.

Test A

In Test A, five needles were prepared for penetration testing. The needles were made from ETHALLOY® Alloy stainless steel and had a diameter of 0.0105 inches. A base coating composition was prepared from a mixture of 20 wt. % of Micropro 600 and Micromatte 2000, produced by Micropowders Inc., mixed with 80 wt. % of HFE-72DE solvent. The MicroPro and Micromatte powder weight ratio was at 4:1. Five test needles were each dipped into the base coating to coat their surfaces. The needles were coated by hand via the dipping process and placed on a magnetic tray. The tray includes raised magnetic strips for holding the proximal ends of the needles secure during the curing cycle and transport while the distal end (tip) of the needles hang over the edge of the magnetic strips. This configuration prevents the needle tips from making contact with the tray. The coated needles were then heated to 190 degrees Celsius in a convection oven Test B In Test B, five needles were prepared for penetration testing. The needles were made from ETHALLOY® Alloy stainless steel and had a diameter of 0.0105 inches. A base coating composition was prepared from a mixture of 20 wt. % of Micropro 600 and Micromatte 2000, produced by Micropowders Inc., mixed with 80 wt. % of HFE-72DE solvent. The MicroPro and Micromatte powder weight ratio was at 4:1. The five test needles were swirl coated with the base coating composition using a single pass spray using the SC-300 Swirl Coat™ Applicator and the Century® C-341 Conformal Coating System available from Asymtek® of Carlsbad, Calif. with the following parameters: 2 PSI fluid pressure, 50 PSI air assist, and 10 in/sec line speed. The coated needles were then heated to 190 degrees Celsius in a convection oven and cured for ninety minutes at ambient atmosphere. The needles were allowed to cool at ambient temperature outside of the oven.

A top coating composition was prepared using 26 wt. % of NuSil® MED4162 with 74 wt. % HFE-72DE solvent. The five test needles were swirl coated with the top coating composition using a single pass spray with the following parameters: 10 PSI fluid pressure, 50 PSI air assist, and 5 in/sec line speed. The needles were then cured for four hours at 220 degrees Celsius. Once cured, the five needles were each passed through the penetration membrane thirty times and the penetration force in grams was recorded as shown in Table 2 below.

TABLE 2

| Experiment | Needle | Pass --> Penetration (g) | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| B | 1 | 30 | 29 | 30 | 31 | 31 | 31 | 33 | 33 | 31 | 32 | 34 | 34 | 34 | 35 | 36 |
| | 2 | 33 | 32 | 31 | 35 | 33 | 34 | 34 | 35 | 34 | 35 | 35 | 36 | 36 | 35 | 37 |
| | 3 | 29 | 28 | 30 | 29 | 30 | 30 | 31 | 31 | 32 | 32 | 32 | 33 | 34 | 32 | 32 |
| | 4 | 29 | 29 | 29 | 28 | 29 | 30 | 31 | 30 | 32 | 33 | 33 | 33 | 35 | 35 | 34 |
| | 5 | 32 | 31 | 33 | 33 | 32 | 32 | 35 | 34 | 34 | 33 | 34 | 35 | 36 | 35 | 36 |
| | St Dev | 1.8 | 1.6 | 1.5 | 2.9 | 1.6 | 1.7 | 1.8 | 2.1 | 1.3 | 1.2 | 1.1 | 1.3 | 1.0 | 1.3 | 2.0 |
| | Avg | 30.6 | 29.8 | 30.6 | 31.2 | 31.0 | 31.4 | 32.8 | 32.6 | 32.6 | 33.0 | 33.6 | 34.2 | 35.0 | 34.4 | 35.0 |
| Experiment | Needle | 16 | 17 | 18 | 19 | 20 | 21 | 22 | 23 | 24 | 25 | 26 | 27 | 28 | 29 | 30 |
| B | 1 | 34 | 38 | 37 | 36 | 37 | 38 | 37 | 38 | 37 | 40 | 40 | 39 | 37 | 39 | 42 |
| | 2 | 37 | 37 | 39 | 38 | 38 | 37 | 38 | 39 | 38 | 39 | 40 | 39 | 40 | 40 | 41 |
| | 3 | 35 | 33 | 33 | 34 | 35 | 34 | 35 | 35 | 36 | 35 | 34 | 34 | 36 | 36 | 37 |
| | 4 | 36 | 36 | 37 | 37 | 38 | 38 | 38 | 39 | 39 | 38 | 40 | 41 | 41 | 38 | 41 |
| | 5 | 38 | 36 | 37 | 34 | 37 | 37 | 36 | 37 | 37 | 37 | 39 | 39 | 38 | 39 | 39 |
| | St Dev | 1.6 | 1.9 | 2.2 | 1.8 | 1.2 | 1.6 | 1.3 | 1.7 | 1.1 | 1.9 | 2.6 | 2.6 | 2.1 | 1.5 | 2.0 |
| | Avg | 36.0 | 36.0 | 36.6 | 35.8 | 37.0 | 36.8 | 36.8 | 37.6 | 37.4 | 37.8 | 38.6 | 38.4 | 38.4 | 38.4 | 40.0 |

FIG. 6 is a graphical representation of the averaged results of Tests A and B in direct comparison. The y-axis shows the penetration force in grams needed to pass a needle through the penetration membrane. The x-axis shows the number of passes. The thick solid line represents the needles that were dip coated with the base and top coating compositions, as set forth in Test A, while the thin solid line represents the needles that were swirl coated with the base and top coating compositions, as set forth in Test B.

As can be seen, the needles that were dip coated had an initial penetration force of about 38 g. The penetration force increased steadily over the thirty passes, and the needles required an average maximum force of 61 g after thirty passes. In contrast, the needles that were swirl coated had an initial penetration force of about 31 g. The penetration force remained substantially constant over the thirty passes, with the average maximum force after thirty passes being about 40 g. As shown, the needles that were swirl coated required about 7 g less force in the beginning on average than the needles that were dip coated, and the force remained substantially constant. Ultimately, the swirl coated needles required about 21 g less maximum force after thirty passes than the dip coated needles.

Example 2

The penetration performance of various coating compositions and coating methods were also tested. In the following Tests A and B, two different types of needle coating compositions and application methods were examined. The needles were passed through Monmouth rubber synthetic media.

Test A

In Test A, ten commercially available Ethicon BV-175 surgical needles having a 0.0078 inch diameter were tested. A coating was applied using a double dipping procedure. In particular, a silicone dip was prepared using a concentration of NuSil® Product No. MED4162 mixed with Micropro 600 and Micromatte 2000 powders for lubrication as described above. The needles were placed on a moving carrier strip and dipped a first time. The needles were then flash cured in a hot box at approximately 225 degrees Celsius for thirty seconds. The needles were then cured for 36 hours in a convection oven at 163 degrees Celsius. The needles were dipped a second time, flash cured, and then cured in a convection oven for another 36 hours.

As shown in Table 3 below, ten needles were tested with thirty passes through the penetration membrane.

TABLE 3

| Experiment | Needle | Pass --> Penetration (g) | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| A | 1 | 35 | 38 | 37 | 38 | 38 | 38 | 38 | 39 | 38 | 38 | 40 | 40 | 41 | 42 | 41 |
| | 2 | 35 | 37 | 37 | 37 | 38 | 39 | 40 | 40 | 39 | 40 | 38 | 40 | 41 | 40 | 39 |
| | 3 | 26 | 26 | 27 | 28 | 28 | 28 | 28 | 29 | 29 | 30 | 31 | 31 | 31 | 30 | 34 |
| | 4 | 28 | 29 | 31 | 32 | 32 | 32 | 32 | 33 | 33 | 33 | 34 | 34 | 34 | 33 | 34 |
| | 5 | 28 | 34 | 31 | 32 | 33 | 34 | 35 | 34 | 34 | 34 | 34 | 35 | 35 | 35 | 36 |
| | 6 | 27 | 28 | 28 | 31 | 30 | 30 | 31 | 32 | 32 | 32 | 34 | 34 | 35 | 32 | 34 |
| | 7 | 34 | 35 | 36 | 37 | 38 | 37 | 38 | 38 | 38 | 39 | 39 | 40 | 40 | 39 | 41 |
| | 8 | 27 | 34 | 32 | 33 | 34 | 34 | 35 | 35 | 36 | 37 | 38 | 37 | 40 | 39 | 38 |
| | 9 | 25 | 28 | 27 | 29 | 30 | 31 | 31 | 33 | 34 | 35 | 35 | 36 | 37 | 37 | 36 |
| | 10 | 25 | 27 | 29 | 30 | 29 | 31 | 31 | 30 | 31 | 31 | 31 | 32 | 32 | 33 | 34 |
| | St Dev | 4.1 | 4.5 | 4.0 | 3.5 | 3.9 | 3.7 | 3.9 | 3.7 | 3.3 | 3.5 | 3.2 | 3.3 | 3.7 | 4.0 | 2.9 |
| | Avg | 29.0 | 31.6 | 31.5 | 32.7 | 33.0 | 33.4 | 33.9 | 34.3 | 34.4 | 34.9 | 35.4 | 35.9 | 36.6 | 36.0 | 36.7 |
| Experiment | Needle | 16 | 17 | 18 | 19 | 20 | 21 | 22 | 23 | 24 | 25 | 26 | 27 | 28 | 29 | 30 |
| A | 1 | 40 | 40 | 42 | 43 | 42 | 40 | 42 | 42 | 43 | 42 | 44 | 43 | 41 | 40 | 43 |
| | 2 | 44 | 39 | 43 | 39 | 41 | 40 | 40 | 44 | 40 | 43 | 42 | 40 | 40 | 42 | 40 |
| | 3 | 31 | 33 | 30 | 32 | 34 | 33 | 33 | 34 | 35 | 34 | 33 | 34 | 35 | 34 | 35 |
| | 4 | 36 | 35 | 36 | 37 | 38 | 37 | 36 | 35 | 36 | 38 | 38 | 38 | 38 | 38 | 38 |
| | 5 | 36 | 35 | 36 | 38 | 37 | 37 | 37 | 38 | 38 | 40 | 38 | 39 | 36 | 38 | 38 |

TABLE 3-continued

| Pass --> | Penetration (g) | | | | | | | | | | | | | | |
|---|---|---|---|---|---|---|---|---|---|---|---|---|---|---|---|
| 6 | 35 | 33 | 35 | 35 | 36 | 34 | 35 | 35 | 35 | 36 | 36 | 36 | 36 | 36 | 36 |
| 7 | 41 | 41 | 40 | 40 | 40 | 41 | 41 | 42 | 42 | 40 | 42 | 42 | 45 | 41 | 41 |
| 8 | 39 | 41 | 40 | 39 | 40 | 40 | 41 | 42 | 40 | 40 | 42 | 43 | 43 | 40 | 40 |
| 9 | 38 | 40 | 39 | 40 | 42 | 42 | 42 | 43 | 43 | 46 | 46 | 43 | 45 | 46 | 46 |
| 10 | 34 | 33 | 34 | 33 | 34 | 33 | 34 | 34 | 34 | 35 | 34 | 34 | 36 | 36 | 34 |
| St Dev | 3.8 | 3.5 | 4.0 | 3.4 | 3.1 | 3.4 | 3.5 | 4.1 | 3.5 | 3.7 | 4.4 | 3.6 | 3.9 | 3.5 | 3.7 |
| Avg | 37.4 | 37.0 | 37.5 | 37.6 | 38.4 | 37.7 | 38.1 | 38.9 | 38.6 | 39.4 | 39.5 | 39.2 | 39.5 | 39.1 | 39.1 |

Test B

In Test B, ten Ethicon tungsten-rhenium alloy needles having an 0.008 inch diameter were tested. The needles were prepared by applying the Momentive® SS4044P primer coat at room temperature. The primer coat was flash cured at 200 degrees Celsius for 2-3 seconds. A base coating composition was then applied over the primer using swirl coating techniques. The base coating composition was made by combining 27.58 wt. % of Momentive®, vinyl siloxane polymer, product no. MSC2631, with 72.25 wt. % of the HFE 72-DE solvent and agitated for about five minutes. Momentive®, catalyst in toluene, product no. SS8010, was then added to the mixture at 0.02 wt. %, and Momentive®, polymethyl hydrogen siloxane, product no. SS4300 was added at 0.14 wt. %. The base coating was applied to the surgical needles using the Asymtek C-341 Conformal Coater and the Asymtek SC-300 Swirl Applicator. The needles were then heated to 300 degrees Celsius for thirty seconds in an infrared heater.

A top coating composition was then applied to the needles and was formed from 26 wt. % of the NuSil® MED4162 silicone product combined with 74 wt. % of the HFE 72-DE solvent. The top coating composition was also applied using swirl coating techniques with the Asymtek C-341 Conformal Coater and the Asymtek SC-300 Swirl Applicator. The needles were again flash cured at a temperature of 190 degrees Celsius for approximately thirty seconds.

The needles included in Test B were then batch cured at 80 degrees Celsius for three hours in a convection oven. The needles were tested by passing each needle thirty times through the penetration membrane. The force required to do so is set forth in Table 4.

TABLE 4

| | Pass --> | Penetration (g) | | | | | | | | | | | | | |
|---|---|---|---|---|---|---|---|---|---|---|---|---|---|---|---|
| Experiment | Needle | 1 | 2 | 3 | 4 | 5 | 6 | 7 | 8 | 9 | 10 | 11 | 12 | 13 | 14 | 15 |
| B | 1 | 22 | 22 | 22 | 23 | 23 | 22 | 22 | 23 | 21 | 23 | 23 | 22 | 22 | 22 | 22 |
| | 2 | 22 | 24 | 23 | 23 | 22 | 21 | 22 | 22 | 22 | 23 | 24 | 23 | 23 | 22 | 23 |
| | 3 | 21 | 21 | 23 | 22 | 21 | 21 | 20 | 22 | 22 | 21 | 22 | 21 | 21 | 22 | 22 |
| | 4 | 21 | 21 | 22 | 22 | 24 | 23 | 24 | 24 | 25 | 23 | 23 | 24 | 24 | 24 | 24 |
| | 5 | 21 | 21 | 22 | 23 | 22 | 22 | 21 | 22 | 21 | 22 | 22 | 22 | 22 | 22 | 22 |
| | 6 | 20 | 22 | 22 | 22 | 22 | 24 | 22 | 22 | 22 | 23 | 23 | 22 | 22 | 22 | 23 |
| | 7 | 21 | 23 | 22 | 22 | 21 | 22 | 22 | 23 | 22 | 23 | 21 | 23 | 22 | 22 | 22 |
| | 8 | 21 | 23 | 22 | 23 | 23 | 23 | 22 | 24 | 23 | 23 | 23 | 23 | 24 | 23 | 23 |
| | 9 | 24 | 24 | 21 | 23 | 23 | 23 | 23 | 23 | 23 | 23 | 23 | 23 | 24 | 25 | 24 |
| | 10 | 21 | 21 | 21 | 20 | 20 | 21 | 21 | 20 | 21 | 21 | 22 | 21 | 21 | 22 | 21 |
| | St Dev | 1.1 | 1.2 | 0.7 | 0.9 | 1.2 | 1.0 | 1.1 | 1.2 | 1.2 | 0.8 | 0.8 | 1.0 | 1.2 | 1.1 | 1.0 |
| | Avg | 21.4 | 22.2 | 22.0 | 22.3 | 22.1 | 22.2 | 21.9 | 22.5 | 22.2 | 22.5 | 22.6 | 22.4 | 22.5 | 22.6 | 22.6 |
| Experiment | Needle | 16 | 17 | 18 | 19 | 20 | 21 | 22 | 23 | 24 | 25 | 26 | 27 | 28 | 29 | 30 |
| B | 1 | 21 | 22 | 23 | 23 | 23 | 22 | 24 | 22 | 22 | 23 | 22 | 23 | 23 | 24 | 23 |
| | 2 | 23 | 24 | 23 | 24 | 24 | 23 | 23 | 24 | 25 | 26 | 26 | 27 | 28 | 29 | 29 |
| | 3 | 22 | 22 | 22 | 22 | 23 | 24 | 24 | 25 | 25 | 25 | 26 | 26 | 26 | 28 | 28 |
| | 4 | 26 | 25 | 24 | 24 | 24 | 24 | 25 | 26 | 25 | 25 | 25 | 26 | 26 | 25 | 26 |
| | 5 | 22 | 22 | 23 | 23 | 23 | 24 | 23 | 22 | 23 | 23 | 23 | 22 | 23 | 25 | 23 |
| | 6 | 23 | 23 | 23 | 23 | 23 | 22 | 24 | 23 | 24 | 24 | 23 | 25 | 24 | 24 | 24 |
| | 7 | 23 | 22 | 23 | 23 | 23 | 24 | 23 | 23 | 23 | 25 | 24 | 23 | 25 | 25 | 24 |
| | 8 | 22 | 23 | 23 | 24 | 24 | 24 | 24 | 24 | 24 | 24 | 23 | 27 | 25 | 25 | 25 |
| | 9 | 24 | 24 | 25 | 24 | 24 | 24 | 24 | 24 | 25 | 25 | 25 | 25 | 26 | 26 | 26 |
| | 10 | 22 | 22 | 21 | 22 | 22 | 22 | 22 | 22 | 23 | 22 | 23 | 23 | 24 | 24 | 23 |
| | St Dev | 1.4 | 1.1 | 1.1 | 0.8 | 0.7 | 0.9 | 0.8 | 1.4 | 1.1 | 1.2 | 1.4 | 1.8 | 1.6 | 1.7 | 2.1 |
| | Avg | 22.8 | 22.9 | 23.0 | 23.2 | 23.3 | 23.3 | 23.6 | 23.5 | 23.9 | 24.2 | 24.0 | 24.7 | 25.0 | 25.5 | 25.1 |

FIG. 7 is a graphical representation of the averaged results of Tests A and B in direct comparison. The y-axis shows the penetration force in grams needed to pass a needle through the penetration membrane. The x-axis shows the number of passes. The thick solid line represents the needles with conventional dip coating, as set forth in Test A, while the thin solid line represents the needles with the spray coating according to the present invention, as set forth in Test B.

As shown, the Test A needles initially required an average penetration force of about 29 g. The average penetration force for the Test A needles increased to 39 g after thirty passes. The Test B needles had an initial average penetration force of 21 g and an average penetration force of 25 g after thirty passes.

Example 3

The following tests were performed to examine the effect coating methods have on the force required to pass a needle through Monmouth rubber synthetic media. The performance of needles that were dip coated was compared with the performance of needles that were spray/swirl coated.

Test A

In Test A, four 0.026 inch diameter needles made from ETHALLOY® Alloy and having a taper cut point geometry were prepared for penetration testing. A base coating composition was prepared from a solution of 2.5 g of Momentive®, vinyl siloxane polymer, product no. MSC2631, 22.15 g of Exxon Isopar-K, 0.0022g of Momentive®, catalyst in toluene, product no. SS8010, and 0.0127 of Momentive®, polymethyl hydrogen siloxane, product no. SS4300. Four test needles were each dipped into the base coating composition to coat their surfaces. The coated needles were then heated to 200 degrees Celsius in a convection oven furnace for one hour.

A top coat coating composition was prepared using 2.50 g of NuSil® MED4162 with 22.50 g of Exxon Isopar-K. The four needles were then each dipped into the top coating composition. The needles where then heated to 140 degrees Celsius in a convection oven and cured for three hours.

Once cured, the four needles were each passed through the penetration membrane thirty times and the penetration force in grams was recorded as shown in Table 5 below.

TABLE 5

| A Needle | Pass → | | | | | | | | | | | | | Penetration (g) | | | | | | | | | | | | | | | | |
|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
| 1 | 61 | 71 | 78 | 84 | 88 | 95 | 97 | 101 | 100 | 104 | 108 | 110 | 110 | 109 | 110 | 111 | 111 | 112 | 110 | 112 | 114 | 112 | 113 | 113 | 112 | 116 | 114 | 113 | 111 | 112 |
| 2 | 65 | 67 | 70 | 73 | 76 | 79 | 82 | 83 | 84 | 84 | 86 | 90 | 90 | 90 | 90 | 92 | 93 | 95 | 95 | 95 | 96 | 96 | 98 | 99 | 102 | 102 | 104 | 104 | 104 | 107 | 109 |
| 3 | 60 | 69 | 75 | 80 | 85 | 88 | 92 | 94 | 95 | 98 | 99 | 100 | 102 | 102 | 103 | 101 | 101 | 104 | 107 | 104 | 103 | 104 | 104 | 103 | 105 | 107 | 107 | 105 | 108 | 108 |
| 4 | 62 | 65 | 69 | 73 | 76 | 79 | 82 | 84 | 86 | 88 | 89 | 92 | 92 | 94 | 95 | 95 | 95 | 97 | 124 | 121 | 122 | 125 | 123 | 127 | 127 | 129 | 130 | 133 | 136 | 132 |
| STDEV | 2 | 3 | 4 | 5 | 6 | 8 | 8 | 9 | 8 | 9 | 10 | 9 | 9 | 8 | 9 | 8 | 8 | 8 | 12 | 11 | 12 | 12 | 11 | 12 | 11 | 11 | 12 | 13 | 14 | 11 |
| AVG | 62 | 68 | 73 | 78 | 81 | 85 | 88 | 91 | 91 | 94 | 96 | 98 | 99 | 99 | 100 | 100 | 100 | 102 | 109 | 108 | 109 | 110 | 110 | 111 | 112 | 114 | 114 | 114 | 116 | 115 |

Test B

In Test B, five 0.026 inch diameter needles made from ETHALLOY® Alloy and having a taper cut point geometry were prepared for penetration testing. The needles were prepared by applying a base coating composition using swirl coating techniques. The base coating composition was made by combining 27.58 wt. % of the Momentive®, vinyl siloxane polymer, product no. MSC2631, with 72.25 wt. % of the HFE 72-DE solvent and agitated for about five minutes. Momentive®, catalyst in toluene, product no. SS8010, was then added to the mixture at 0.02 wt. %, and Momentive®, polymethyl hydrogen siloxane, product no. SS4300 was added at 0.14 wt. %. The base coating was applied to the surgical needles using the Asymtek C-341 Conformal Coater and the Asymtek SC-300 Swirl Applicator. The needles were then heated to 300 degrees Celsius for thirty seconds in an infrared heater.

A top coating composition was then applied to the needles and was formed from 26 wt. % of the NuSil® MED4162 silicone product combined with 74 wt. % of the HFE 72-DE solvent. The top coating composition was also applied using swirl coating techniques with the Asymtek C-341 Conformal Coater and the Asymtek SC-300 Swirl Applicator. The needles included in Test B were then batch cured at 140 degrees Celsius for three hours in a convection oven.

Once cured, the five needles were each passed through a Monmouth rubber synthetic media thirty times and the penetration force in grams was recorded as shown in Table 6 below.

TABLE 6

| B Needle | Pass → | | | | | | | | Penetration (g) | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| 1 | 66 | 69 | 70 | 70 | 71 | 70 | 70 | 72 | 70 | 70 | 72 | 71 | 72 | 72 | 74 | 74 |
| 2 | 58 | 60 | 60 | 61 | 61 | 61 | 63 | 62 | 63 | 62 | 63 | 64 | 64 | 64 | 62 | 64 |
| 3 | 56 | 56 | 57 | 57 | 58 | 58 | 58 | 58 | 54 | 53 | 53 | 53 | 53 | 53 | 53 | 53 |
| 4 | 53 | 54 | 55 | 56 | 56 | 56 | 56 | 56 | 56 | 56 | 57 | 57 | 58 | 58 | 58 | 58 |
| 5 | 56 | 57 | 59 | 61 | 56 | 57 | 58 | 59 | 58 | 59 | 60 | 60 | 60 | 59 | 57 | 59 |
| STDEV | 4.9 | 5.9 | 5.8 | 5.5 | 6.3 | 5.7 | 5.7 | 6.3 | 6.4 | 6.5 | 7.2 | 6.9 | 7.1 | 7.2 | 8.0 | 8.0 |
| AVG | 58 | 59 | 60 | 61 | 60 | 60 | 61 | 61 | 60 | 60 | 61 | 61 | 61 | 61 | 61 | 62 |

TABLE 6-continued

| B | Pass → | Penetration (g) | | | | | | | | | | | | | |
|---|---|---|---|---|---|---|---|---|---|---|---|---|---|---|
| | Needle | 17 | 18 | 19 | 20 | 21 | 22 | 23 | 24 | 25 | 26 | 27 | 28 | 29 | 30 |
| | 1 | 75 | 76 | 76 | 76 | 76 | 76 | 76 | 75 | 76 | 74 | 75 | 74 | 73 | 73 |
| | 2 | 66 | 65 | 66 | 67 | 68 | 68 | 63 | 63 | 61 | 64 | 65 | 66 | 68 | 68 |
| | 3 | 53 | 53 | 53 | 54 | 54 | 54 | 55 | 55 | 55 | 56 | 56 | 56 | 57 | 58 |
| | 4 | 58 | 58 | 58 | 58 | 60 | 60 | 59 | 60 | 60 | 60 | 60 | 61 | 61 | 61 |
| | 5 | 59 | 60 | 60 | 61 | 60 | 61 | 61 | 62 | 62 | 62 | 62 | 63 | 62 | 62 |
| | STDEV | 8.5 | 8.7 | 8.8 | 8.6 | 8.5 | 8.4 | 7.9 | 7.4 | 7.9 | 6.7 | 7.2 | 6.7 | 6.3 | 6.0 |
| | AVG | 62 | 62 | 63 | 63 | 64 | 64 | 63 | 63 | 63 | 63 | 64 | 64 | 64 | 64 |

FIG. 8 is a graphical representation of the averaged results of Tests A and B in direct comparison. The y-axis shows the penetration force in grams needed to pass a needle through the penetration membrane. The x-axis shows the number of passes. The square points represent the needles with the dip coating, as set forth in Test A, while the diamond points represent the needles with the spray coating according to the present invention, as set forth in Test B.

As shown, the Test A needles with the dip coating initially required an average penetration force of 62 g. The average penetration force for the Test A needles increased to 115 g after thirty passes. The Test B needles with the spray coating performed with an initial average penetration force of 58 g and resulted in an average penetration force of 64 g after thirty passes. As can be seen, the needles in Test B with the spray coating required significantly less penetration force up to thirty passes.

Example 4

The penetration performance of various coating compositions and coating methods were tested. In the following Tests A, B, and C, three different types of needle coating compositions and application methods were examined. The penetration material for these tests was human cadaver carotid artery tissue.

Test A

In Test A, commercially available Ethicon BV-1 surgical needles having a 0.0105 inch diameter were tested. A coating was applied using the procedures associated with the manufacture of this series. In particular, a silicone dip was prepared using a concentration of NuSil® Product No. MED4162. The needles were placed on a moving carrier strip and dipped a first time. The needles were then flash cured in a hot box at approximately 190 degrees Celsius for twenty seconds. The needles were dipped a second time and flash cured again at the same settings as above. Finally, the needles were dipped a third time and then cured in a convection oven for 8 to 16 hours at 190 degrees Celsius.

Test B

In Test B, Ethicon tungsten-rhenium alloy needles having a 0.0105 inch diameter were tested. The needles were prepared by applying the Momentive® SS4044P primer coat at room temperature. A base coating composition was then applied over the primer using swirl coating techniques. The base coating composition was made by combining 27.58 wt. % of the Momentive®, vinyl siloxane polymer, product no. MSC2631, with 72.25 wt. % of the HFE 72-DE solvent and agitated for about five minutes. Momentive®, catalyst in toluene, product no. SS8010, was then added to the mixture at 0.02 wt. %, and Momentive®, polymethyl hydrogen siloxane, product no. SS4300, was added at 0.14 wt. %. The base coating was applied to the surgical needles using the Asymtek C-341 Conformal Coater and the Asymtek SC-300 Swirl Applicator. The needles were then heated to 300 degrees Celsius for thirty seconds in an infrared heater.

A top coating composition was then applied to the needles and was formed from 26 wt. % of the NuSil® MED4162 silicone product combined with 74 wt. % of the HFE 72-DE solvent. The top coating composition was also applied using swirl coating techniques with the Asymtek C-341 Conformal Coater and the Asymtek SC-300 Swirl Applicator.

The needles included in Test B were then batch cured at 80 degrees Celsius for three hours in a convection oven. The needles were tested by passing each needle thirty times through the penetration membrane.

Test C

In Test C, a competing brand of commercially available surgical needles (0.010 inch diameter) was tested out of the package. The needles were tested by passing each needle thirty times through the penetration membrane.

FIG. 9 is a graphical representation of the averaged results of Tests A, B, and C in direct comparison. The y-axis shows the penetration force in grams needed to pass a needle through human cadaver tissue. The x-axis shows the number of passes. The triangular points represent the needles with the conventional dip coating, as set forth in Test A above. The circular points represent the needles prepared according to the present invention as forth in Test B above. The diamond points represent the competing brand of needles as set forth in Test C above.

As shown, the commercially available Test A needles having a dip coating initially required an average penetration force of about 16 g. The average penetration force for the Test A needles increased to about 18 g after thirty passes. The Test B needles with the coating according to the present invention performed with an initial average penetration force of about 13 g and maintained this penetration force after thirty passes. The competing brand of needles performed with an initial average penetration force of about 15 g and resulted in an average penetration force of about 25 g after thirty passes. As can be seen, the needles in Test B required significantly less penetration force up to thirty passes.

The use of two coatings as described above with respect to the present invention results in surgical needles that exhibit reduced tissue penetration force compared with standard surgical needles after an equivalent number of passes through tissue. Thus, both the lubricity of the needle as well as the durability of the coating is improved. This is believed to result for a number of reasons. For example, application of the base and top coats using a swirl coating process provides an even distribution of the coatings over the substrate. Furthermore, the composition of the coatings in combination with the methods of application and curing can result in significantly decreased average force required to repeatedly pass the needle through tissue. The curing time is also significantly decreased, resulted in more efficient manufacturing processes.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for coating a surgical needle, comprising:
    applying, as a liquid, a primer coat to a surgical needle formed from a tungsten-rhenium alloy such that the primer coat at least partially covalently bonds with the tungsten-rhenium alloy;
    applying a base coat onto the primer coat, the base coat bonding with the primer coat; and
    applying a top coat onto the base coat, the top coat bonding with the base coat, wherein the base coat comprises a vinyl functionalized organopolysiloxane and a hydrofluoroether solvent, and the top coat comprises a polydimethylsiloxane and a hydrofluoroether solvent.

2. The method of claim 1, wherein the base coat and the top coat are applied by spray-coating.

3. The method of claim 1, wherein the primer coat comprises a silicone.

4. The method of claim 1, wherein a force required to penetrate the surgical needle through tissue remains substantially constant when the surgical needle is passed through tissue at least about thirty times.

5. The method of claim 1, further comprising curing the primer coat after applying the primer coat to the surgical needle as a liquid.

6. The method of claim 1, further comprising applying the base coat, as a liquid, onto the primer coat.

7. The method of claim 6, further comprising curing the base coat after applying the base coat onto the primer coat as a liquid.

8. The method of claim 1, further comprising:
    curing the primer coat after applying the primer coat to the surgical needle as a liquid;
    applying the base coat, as a liquid, onto the primer coat; and
    curing the base coat after applying the base coat onto the primer coat as a liquid.

9. The method of claim 1, wherein the primer coat comprises polyalkylsiloxane and tetraethyl silicate.

10. The method of claim 1, wherein the primer coat has a thickness in a range of approximately 0.01 µm to approximately 1 µm.

* * * * *